United States Patent
Pavlov et al.

(10) Patent No.: US 11,103,195 B2
(45) Date of Patent: Aug. 31, 2021

(54) METHOD FOR PROVIDING EATING HABIT INFORMATION AND WEARABLE DEVICE THEREFOR

(71) Applicant: SAMSUNG ELECTRONICS CO., LTD., Suwon-si (KR)

(72) Inventors: Konstantin Alexandrovich Pavlov, Moscow (RU); Alexey Andreevich Gavron, Yaroslavskaya oblast (RU); Alexander Nikolaevich Khripkov, Moscow (RU); Stanislav Vladimirovich Polonsky, Moscow (RU); Maxim Alexeevich Vilenskii, Moscow (RU); Jae-geol Cho, Yongin-si (KR); Young-hyun Kim, Suwon-si (KR); Ah-young Choi, Seoul (KR)

(73) Assignee: SAMSUNG ELECTRONICS CO., LTD., Suwon-si (KR)

(*) Notice: Subject to any disclaimer, the term of this patent is extended or adjusted under 35 U.S.C. 154(b) by 386 days.

(21) Appl. No.: 15/775,590

(22) PCT Filed: Aug. 26, 2016

(86) PCT No.: PCT/KR2016/009522
§ 371 (c)(1),
(2) Date: May 11, 2018

(87) PCT Pub. No.: WO2017/082525
PCT Pub. Date: May 18, 2017

(65) Prior Publication Data
US 2018/0344259 A1    Dec. 6, 2018

(30) Foreign Application Priority Data

Nov. 11, 2015 (RU) .......................... RU2015148522
Aug. 19, 2016 (KR) ...................... 10-2016-0105584

(51) Int. Cl.
G09B 23/28 (2006.01)
A61B 5/00 (2006.01)
(Continued)

(52) U.S. Cl.
CPC .......... *A61B 5/7275* (2013.01); *A61B 5/0002* (2013.01); *A61B 5/02055* (2013.01);
(Continued)

(58) Field of Classification Search
CPC .......... G09B 23/28; A61B 5/02; A61B 5/026; A61B 5/0261; A61B 5/14532
(Continued)

(56) References Cited

U.S. PATENT DOCUMENTS 6,841,389 B2   1/2005   Novikov et al.
7,050,847 B2   5/2006   Ollmar et al.
(Continued)

FOREIGN PATENT DOCUMENTS

CN   1471373 A   1/2004
CN   1522124 A   8/2004
(Continued)

OTHER PUBLICATIONS

International Search Report (PCT/ISA/210) dated Dec. 5, 2016 issued by the International Searching Authority in International Application No. PCT/KR2016/009522.
(Continued)

*Primary Examiner* — Kurt Fernstrom
(74) *Attorney, Agent, or Firm* — Sughrue Mion, PLLC

(57) ABSTRACT

Disclosed is a wearable device comprising: an impedance sensor for measuring an impedance signal inside a user's body; and a controller for determining the number of meals for a predetermined period and the glycemic index corresponding to each meal using the measured impedance signal
(Continued)

and providing the user's eating habit information on the basis of the number of meals and the glycemic index.

17 Claims, 21 Drawing Sheets

(51) Int. Cl.
| | |
|---|---|
| A61B 5/145 | (2006.01) |
| G16H 50/20 | (2018.01) |
| A61B 5/0531 | (2021.01) |
| G16H 40/63 | (2018.01) |
| G16H 20/60 | (2018.01) |
| A61B 5/0205 | (2006.01) |
| A61B 5/01 | (2006.01) |
| A61B 5/021 | (2006.01) |
| A61B 5/024 | (2006.01) |
| A61B 5/053 | (2021.01) |
| A61B 5/11 | (2006.01) |

(52) U.S. Cl.
CPC ........ *A61B 5/0531* (2013.01); *A61B 5/14532* (2013.01); *A61B 5/4266* (2013.01); *A61B 5/442* (2013.01); *A61B 5/486* (2013.01); *A61B 5/4866* (2013.01); *A61B 5/681* (2013.01); *A61B 5/746* (2013.01); *A61B 5/7475* (2013.01); *G16H 20/60* (2018.01); *G16H 40/63* (2018.01); *G16H 50/20* (2018.01); *A61B 5/0059* (2013.01); *A61B 5/01* (2013.01); *A61B 5/021* (2013.01); *A61B 5/02438* (2013.01); *A61B 5/053* (2013.01); *A61B 5/1118* (2013.01); *A61B 5/742* (2013.01); *A61B 5/7405* (2013.01); *A61B 5/7455* (2013.01); *A61B 2562/029* (2013.01); *A61B 2562/0209* (2013.01)

(58) Field of Classification Search
USPC ............. 434/127, 262; 340/539.12; 600/301, 600/309, 365
See application file for complete search history.

(56) References Cited

U.S. PATENT DOCUMENTS

| | | | |
|---|---|---|---|
| 7,182,248 B2 | 2/2007 | Ookushi | |
| 7,840,269 B2 | 11/2010 | Policker et al. | |
| 8,641,612 B2 | 2/2014 | Teller et al. | |
| 8,968,195 B2 | 3/2015 | Tran | |
| 9,168,000 B2* | 10/2015 | Dunki-Jacobs | A61B 5/4238 |
| 10,667,728 B2 | 2/2020 | Sokolov et al. | |
| 2004/0147816 A1* | 7/2004 | Policker | A61B 5/42 |
| | | | 600/300 |
| 2004/0215068 A1* | 10/2004 | Lykke | A61B 5/07 |
| | | | 600/302 |
| 2005/0096514 A1* | 5/2005 | Starkebaum | A61B 5/04 |
| | | | 600/309 |
| 2010/0047745 A1 | 2/2010 | Bergqwist et al. | |
| 2010/0305468 A1* | 12/2010 | Policker | A61F 5/0059 |
| | | | 600/547 |
| 2010/0324432 A1* | 12/2010 | Bjorling | A61N 1/36007 |
| | | | 600/504 |
| 2011/0028803 A1 | 2/2011 | Ollmar | |
| 2011/0053121 A1* | 3/2011 | Heaton | G16H 20/60 |
| | | | 434/127 |
| 2011/0152658 A1 | 6/2011 | Peyser et al. | |
| 2011/0301446 A1* | 12/2011 | Kamen | G16H 20/40 |
| | | | 600/365 |
| 2012/0277619 A1* | 11/2012 | Starkebaum | A61B 5/6871 |
| | | | 600/547 |
| 2016/0012749 A1* | 1/2016 | Connor | G16H 50/30 |
| | | | 600/13 |
| 2016/0117951 A1* | 4/2016 | Fleischer | A61F 5/003 |
| | | | 434/127 |
| 2016/0148535 A1* | 5/2016 | Ashby | A61B 7/008 |
| | | | 434/127 |
| 2016/0262707 A1 | 9/2016 | DeVries | |
| 2017/0164878 A1* | 6/2017 | Connor | A61B 5/4866 |
| 2018/0035930 A1 | 2/2018 | Sokolov et al. | |

FOREIGN PATENT DOCUMENTS

| | | |
|---|---|---|
| CN | 104302229 A | 1/2015 |
| EP | 2 158 838 A1 | 3/2010 |
| EP | 2 818 108 A1 | 12/2014 |
| JP | 2004-523328 A | 8/2004 |
| JP | 2004-302498 A | 10/2004 |
| KR | 10-2009-0043682 A | 5/2009 |
| KR | 10-1440735 B1 | 9/2014 |
| RU | 2 519 955 C1 | 6/2014 |
| RU | 2 521 254 C1 | 6/2014 |
| RU | 2518134 C2 | 6/2014 |
| WO | 2008/009737 A2 | 1/2008 |
| WO | 2013/125987 A1 | 8/2013 |
| WO | 2015/058286 A1 | 4/2015 |

OTHER PUBLICATIONS

Written Opinion (PCT/ISA/237) dated Dec. 5, 2016 issued by the International Searching Authority in International Application No. PCT/KR2016/009522.
Communication dated May 24, 2019, issued by the European Patent Office in counterpart European Application No. 16 864 451.6.
Communication dated Jun. 28, 2018, issued by the European Patent Office in counterpart European Application No. 16864451.6.
Rubin, M. S., et al., "The History and Technology Behind Healbe GoBe (TM)", Apr. 4, 2014, XP055481594, http://www.dinaint.com/upload/files/healbe_historytechnology_0404.pdf, 15 pages total.
Communication dated May 18, 2020, issued by the Intellectual Property Office of P.R. China in counterpart Chinese Application No. 201680065765.0.
Communication dated Mar. 27, 2017 issued by the Russian Patent Office in Russian Application No. 2015148522.
I. Chaikovsky et al., "Non-invasive blood glucose meter: reality and hope", 2013, 10 pages total.
Sandeep Kumar Vashist, "Non-invasive glucose monitoring technology in diabetes management: a review", Anal Chim Acta., 750, Oct. 31, 2012, 1 page total.
Communication dated Feb. 2, 2021 issued by the China National Intellectual Property Administration in Chinese Application No. 201680065765.0.

* cited by examiner

| | Breakfast | Lunch | Dinner |
|---|---|---|---|
| Glycemic index | 80 | 60 | 55 |

METHOD FOR PROVIDING EATING HABIT INFORMATION AND WEARABLE DEVICE THEREFOR

TECHNICAL FIELD

The present disclosure relates to a method and a wearable apparatus for providing eating habits information to a user by analyzing eating habits of the user.

BACKGROUND ART

Obesity is a preventable major cause of death globally among an increasing proportion of adults and children. Obesity may occur most frequently based on a combination of excessive dietary energy consumption and a lack of physical activity.

The main treatment for obesity is a diet and physical exercise. Diet programs may bring about weight loss over a short period of time. However, it is normally difficult to maintain weight loss, and continual individual exercises and low calorie diets are required.

Accordingly, systems for monitoring calorie consumption and eating habits have been developed as a solution. However, there is a need for a method of analyzing and monitoring individual eating habits, such as the number of meals, calories consumed from a meal, a glycemic index (GI) corresponding to each meal consumed by a user, etc.

DESCRIPTION OF EMBODIMENTS

Technical Problem

According to an embodiment, there are provided a method and a wearable apparatus for providing eating habits information of a user based on the number of meals consumed during a predetermined time period and a glycemic index (GI) corresponding to each meal.

A wearable apparatus may include: an impedance sensor configured to measure an impedance signal in a body of a user; and a controller configured to determine, by using the measured impedance signal, a number of meals consumed during a certain time period and a glycemic index (GI) corresponding to each meal, and to provide eating habits information of the user based on the determined number of meals and the determined GI for each meal.

The controller may further be configured to generate a blood sugar curve by using the measured impedance signal and analyze the generated blood sugar curve to determine the number of meals for the certain time period and the GI corresponding to each meal.

The wearable apparatus may further include at least one of a temperature sensor configured to measure a body temperature of the user, a humidity sensor configured to measure an amount of sweating of the user, a reflective optical sensor configured to measure a skin characteristic of the user, a heartbeat sensor configured to measure a heartbeat of the user, a blood pressure sensor configured to measure a blood pressure of the user, and an operation sensor configured to measure an activity of the user. The controller may further be configured to correct the determined GI by taking into account at least one of body temperature information, sweating amount information, skin characteristics information, heartbeat information, blood pressure information, and activity information of the user.

The controller may further be configured to obtain metabolic characteristics information of the user and to correct the determined GI by using the metabolic characteristics information.

The wearable apparatus may further include a user input unit configured to receive, from the user, an input of selecting food to be consumed. The controller may further be configured to determine a blood sugar level corresponding to the selected food by measuring the impedance signal in the body of the user, and to obtain the metabolic characteristics information of the user based on a result of comparing the determined blood sugar level with a standard blood sugar level of the selected food.

The controller may further be configured to determine a level of risk of eating habits of the user based on the eating habits information of the user, and to control an output unit to output a warning notification when the level of risk of the eating habits of the user is greater than a critical value.

The controller may further be configured to control an output unit to output at least one of information about recommendations for improving eating habits, information about exercise recommendations, and information about prediction of a body-shape change based on eating habits improvement, based on the eating habits information of the user.

The controller may further be configured to recommend at least one of a weight management application, a diet application, an exercise management application, and a disease management application, based on the eating habits information of the user.

The wearable apparatus may further include a communicator configured to transmit the eating habits information of the user to an external apparatus.

The impedance sensor may include: a signal source configured to generate an alternating current (AC) power supply having at least two frequency ranges; a probe configured to receive the AC power supply and to transmit an AC signal to the body of the user; and a signal sensor configured to receive the AC signal transmitted by the probe through the body of the user, and to convert the received AC signal into the impedance signal.

The probe may further be configured to transmit the AC signal in at least two directions.

A method of providing eating habits information may include: measuring an impedance signal in a body of a user by using an impedance sensor; determining a number of meals for a certain time period and a glycemic index (GI) corresponding to each meal, by using the measured impedance signal; and providing the eating habits information of the user based on the number of meals and the GI.

The eating habits information of the user may include at least one of information about the number of meals for the certain time period, information about eating intervals, information about eating times, information about an average eating duration time, information about a blood sugar curve, and information about a GI corresponding to each meal.

The determining of the number of meals and the GI may include: generating a blood sugar curve by using the measured impedance signal; and determining the number of meals for the certain time period and the GI corresponding to each meal, by analyzing the blood sugar curve.

The method may further include correcting the determined GI by taking into account at least one of body temperature information, sweating amount information, skin characteristics information, heartbeat information, blood pressure information, and activity information of the user.

The method may further include obtaining metabolic characteristics information of the user and correcting the GI by using the metabolic characteristics information.

The obtaining of the metabolic characteristics information of the user may include: receiving, from the user, an input of selecting food to be consumed; determining a blood sugar level corresponding to the selected food by measuring the impedance signal in the body of the user; and obtaining the metabolic characteristics information of the user based on a result of comparing the determined blood sugar level with a standard blood sugar level of the selected food.

The method may further include based on the eating habits information of the user, outputting at least one of information about recommendations for improving eating habits, information about exercise recommendations, information about prediction of a body-shape change based on eating habits improvement, and information about application recommendations.

The method may further include transmitting the eating habits information of the user to an external apparatus.

A non-transitory computer-readable recording medium may have embodied thereon a program for executing the method of providing the eating habits information.

MODE OF DISCLOSURE

Figure 1:
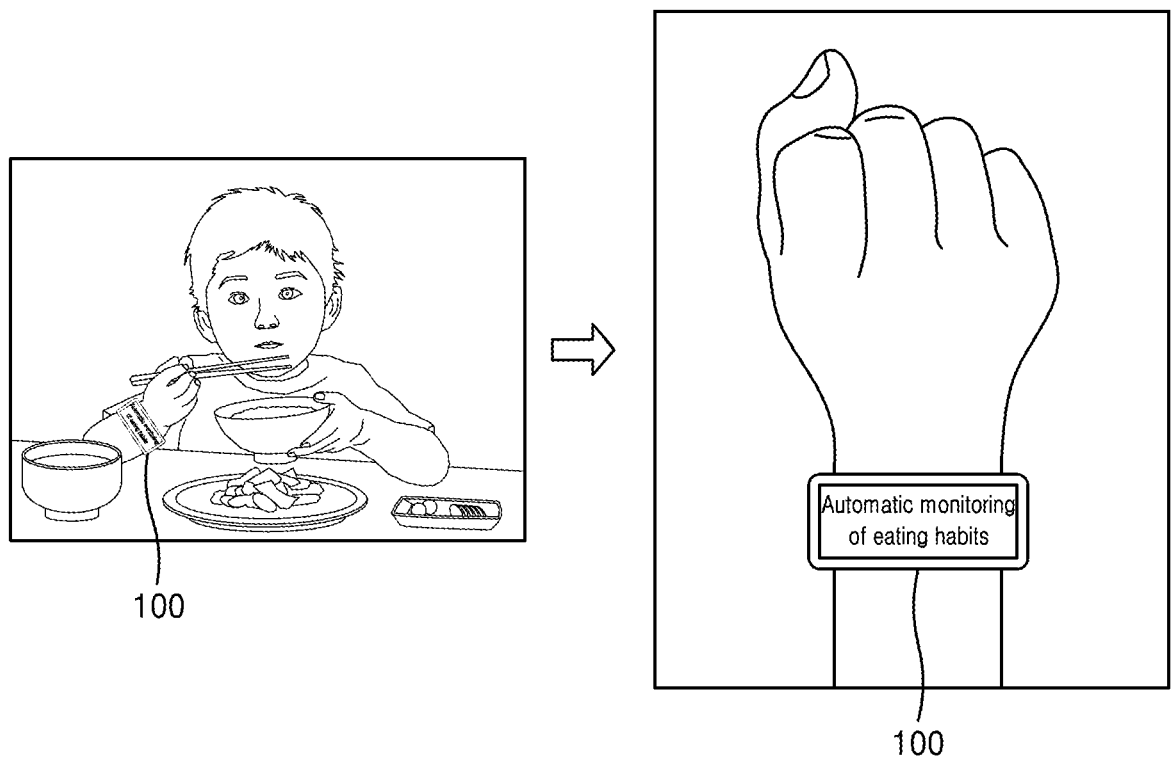
FIG. 1 is a view for schematically describing an operation of a wearable apparatus configured to provide eating habits information, according to an embodiment.
Figure 2:
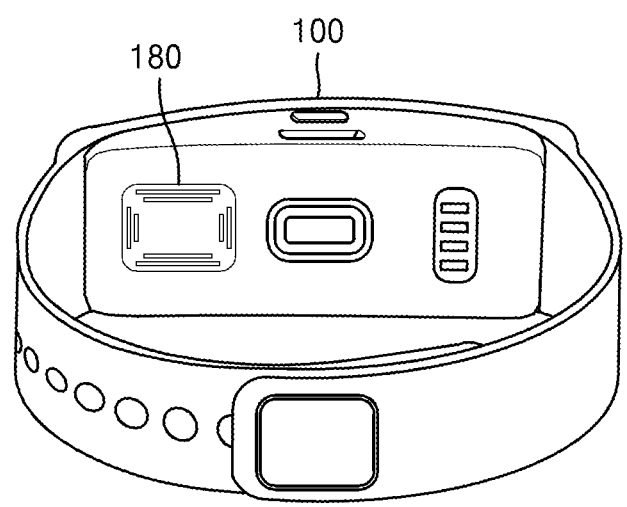
FIG. 2 is a view for describing a wearable apparatus configured to provide eating habits information, according to an embodiment.

FIG. 1 is a view for schematically describing an operation of a wearable apparatus 100 configured to provide eating habits information, according to an embodiment. As illustrated in FIG. 1, the wearable apparatus 100 according to an embodiment may be an apparatus configured to monitor eating habits of a user and provide the eating habits information to the user. The wearable apparatus 100 according to an embodiment may be worn by a user, and may include at least one of an accessory-type apparatus (for example, a watch, a ring, a bracelet, an ankle bracelet, a necklace, glasses, and contact lenses), a head-mounted-device (HMD), a fabric or clothing integrated-type apparatus (for example, electronic clothing), a body-attached device (for example, a skin pad), and a body-implantable circuit. However, the wearable apparatus 100 is not limited thereto. Hereinafter, for convenience of explanation, a case in which the wearable apparatus 100 is a wristband or a wristwatch will be described as an example. According to an embodiment, when a user eats, the wearable apparatus 100 may determine a glycemic index (GI) corresponding to each meal eaten by the user and provide eating habits information of the user based on the GI corresponding to each of the meals. The GI may denote a value generated by comparing a level of increase in blood sugar after consumption of a predetermined amount of a carbohydrate food sample with a level of rise in blood sugar after consumption of the equivalent amount of a standard carbohydrate food. That is, the GI may refer to a value indicating how quickly a specific type of food that is consumed is converted to glucose to increase a blood sugar level, in a digestive process. All types of carbohydrates are absorbed in the body after being converted to glucose. Here, with the blood sugar level (100) of pure glucose as a reference, the GI is a numerical value for easily indicating how much a specific type of food that is consumed on an empty stomach increases a blood sugar level for two hours. That is, the higher the GI with respect to a particular type of food, the faster the particular type of food increases glucose concentrations after being consumed. The reason that the GI is important is because, in addition to calories, a speed of increase in glucose concentrations after consumption of a meal greatly affects various adult diseases, such as obesity, diabetes, breast cancer, etc. A food having high GI stimulates the pancreas and causes the pancreas to release excessive insulin such that the excessive insulin may fatigue the pancreas and cause diabetes. Hereinafter, the wearable apparatus 100 configured to analyze a GI by monitoring a change in blood sugar levels of a user will be described in more detail by referring to FIG. 2. FIG. 2 is a view for describing the wearable apparatus 100 configured to provide eating habits information, according to an embodiment. According to an embodiment, the wearable apparatus 100 may measure a change in blood sugar levels of a user by using an impedance sensor. The change in blood sugar levels in a body of the user may cause a change in potassium and sodium ion concentrations in the blood, and the change in potassium and sodium ion concentrations in the blood may bring a change in a bioimpedance spectrum of the blood. Thus, the wearable apparatus 100 may monitor the change in blood sugar levels of the user, by measuring the change in a bioimpedance spectrum of the blood by using the impedance sensor. As illustrated in FIG. 2, the impedance sensor may include a probe 180 configured to sense a change in an impedance spectrum of the user. According to an embodiment, the probe 180 may be attached to the body of the user. For example, the probe 180 may be attached to the body of the user in a non-contact manner. Alternatively, the probe 180 may be mounted inside leather, rubber, plastic, etc. included in the wearable apparatus 100. The probe 180 may measure the change in an impedance spectrum at an area to which the probe 180 is attached. For example, the probe 180 may measure the change in an impedance spectrum by using an alternating current (AC). The probe 180 may radiate the AC and sense a change in a returning current, so as to sense the change in an impedance spectrum in the body of the user. Hereinafter, an operation performed by the wearable apparatus 100 to measure the change in an impedance spectrum (hereinafter, an impedance signal) by using the probe 180 of the impedance sensor will be described in more detail, by referring to FIGS. 3A through 3C.

Figure 3A:
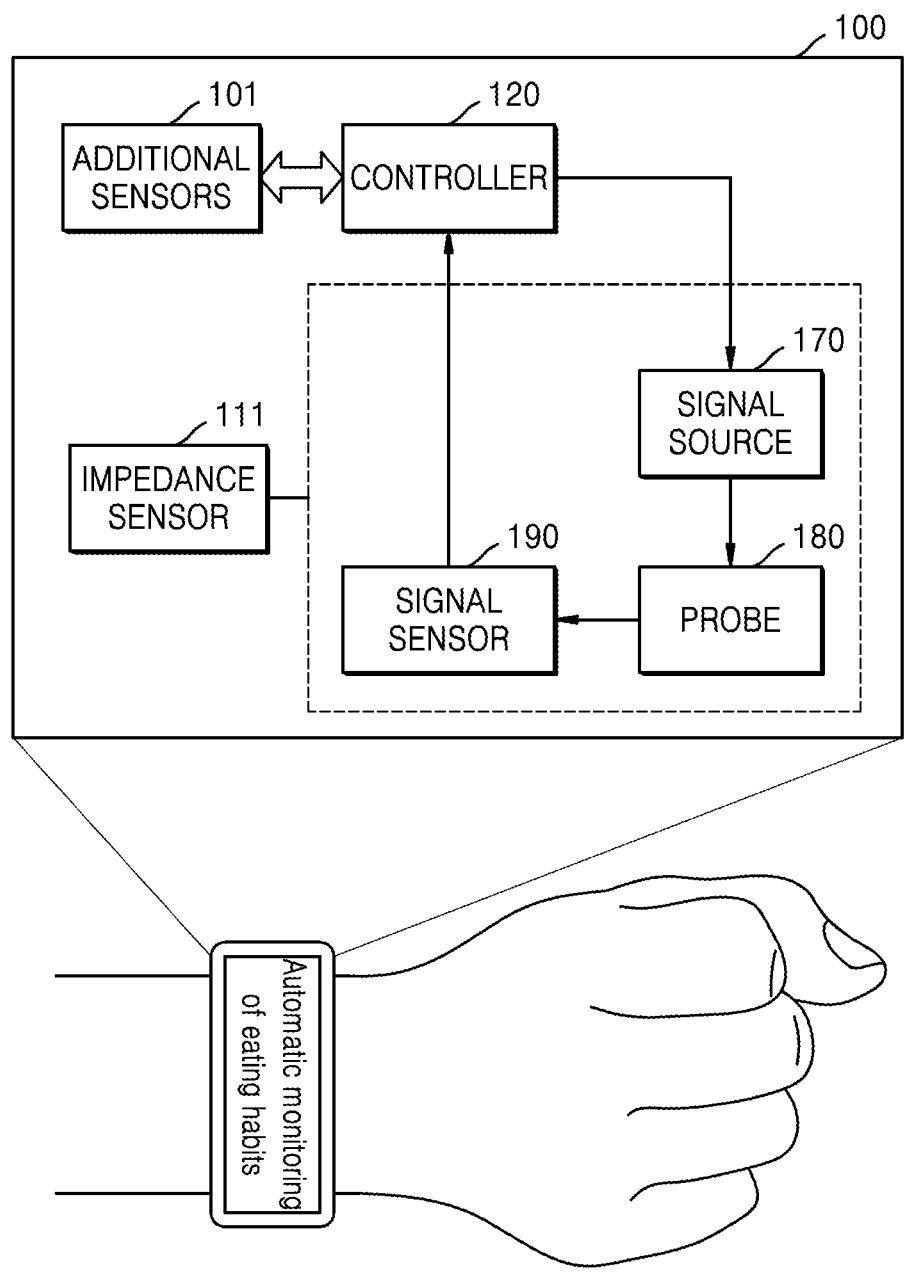
FIGS. 3A through 3C are block diagrams of components of a wearable apparatus, according to an embodiment.
Figure 3B:
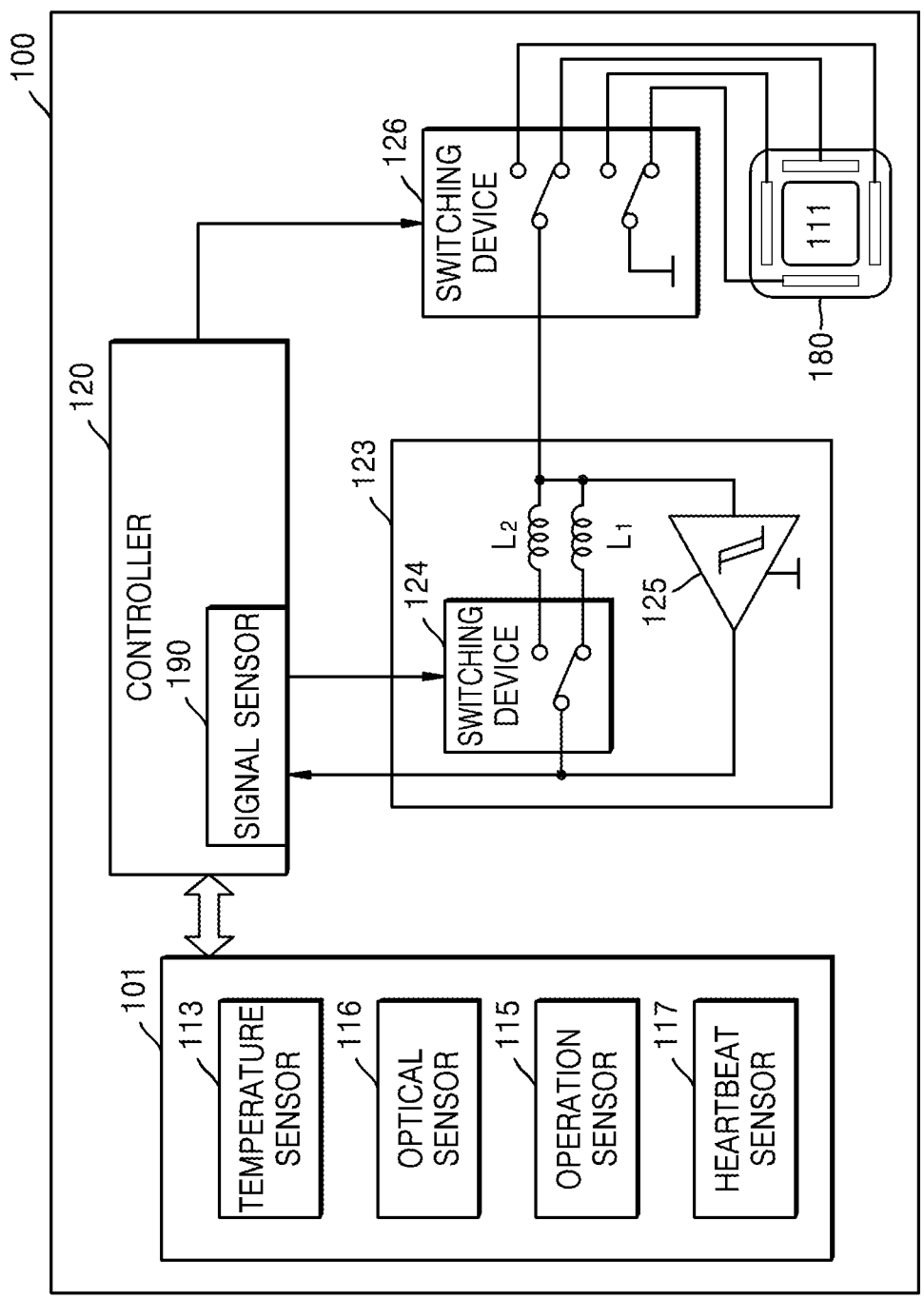
Figure 3C:
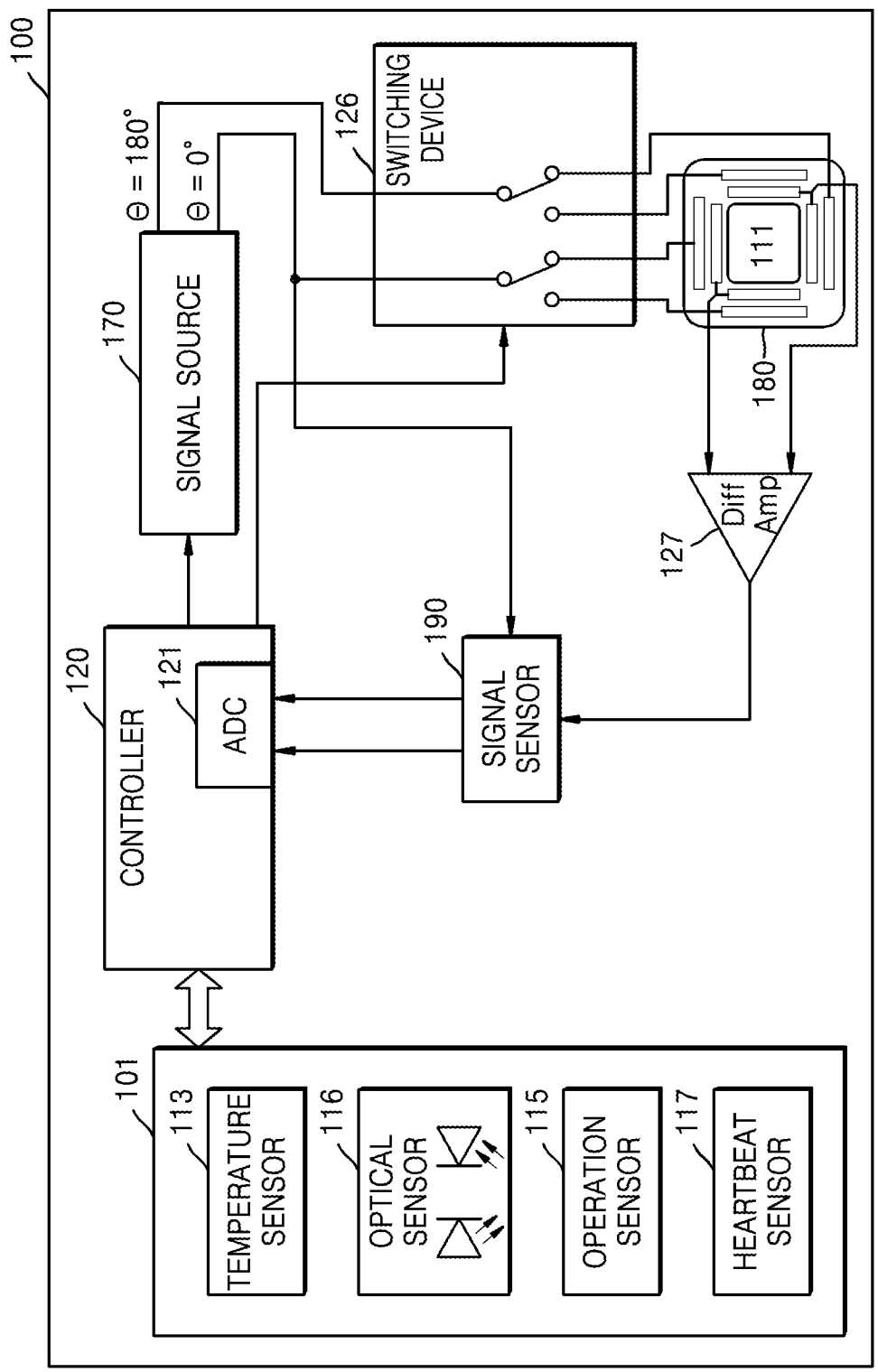

FIGS. 3A through 3C are block diagrams of components of the wearable apparatus 100 according to an embodiment.

As illustrated in FIG. 3A, the wearable apparatus 100 may include, but is not limited to, a controller 120, an impedance sensor 111 configured to measure an impedance signal, and additional sensors 101. Hereinafter, each of the components will be described.

The controller 120 may provide a means for performing control of circuit current, data acquisition and data processing within the wearable device. The controller 120 may be directly connected to a signal source 170, in order to adjust a signal frequency for measuring the impedance signal.

The impedance sensor 111 may include the signal source 170, the probe 180, and a signal sensor 190. For example, the impedance sensor 111 may include the signal source 170 configured to generate an AC power supply having at least two frequency ranges, the probe 180 configured to receive the AC power supply and transmit an AC signal to the body of the user, and the signal sensor 190 configured to receive the AC signal transmitted by the probe 180 through the body of the user and convert the received AC signal to the impedance signal.

The signal source 170 may generate shifting currents having at least two frequency ranges. Here, the frequency ranges may be selected to provide an electrical characteristic difference in the body of the user, the electrical characteristic difference being generated based on a body fluid balance in extracellular and intracellular compartments. According to an embodiment, the first one of the at least two frequency ranges may be selected to be between 10 kHz and 100 kHz, and the second one of the at least two frequency ranges may be selected to be between 500 kHz and 50 MHz.

The signal source 170 may be connected to the probe 180. The probe 180 may transmit a low current to the body of the user. Also, the probe 180 may receive a current returning from the body of the user. According to an embodiment, the probe 180 may be solidly attached to the body of the user. However, a galvanic contact between the probe 180 and the body of the user is not required. For example, the probe 180 may be attached to the body of the user in a non-galvanic contact manner.

The probe 180 may be connected to the signal sensor 190. The signal sensor 190 may convert a signal, having passed through the body of the user, into the impedance signal. Also, according to an embodiment, the signal sensor 190 may be directly connected to the controller 120. The controller 120 may receive, from the signal sensor 190, data with respect to a change in impedance signal generated from the body of the user.

The additional sensors 101 may include one or more bio-sensors or environment sensors. The additional sensors 101 may be controlled by the controller 120. The controller 120 may use the additional sensors 101 in order to filter data unrelated to a change in GI according to consumption of food. For example, the controller 120 may use stress information, physical activity information, physiological information, such as skin reaction against an external condition, etc., which are obtained from the additional sensors 101, in order to correct the GI.

Referring to FIG. 3B, the impedance sensor 111 including the probe 180 may be implemented as a magnetic oscillation circuit. Also, according to an embodiment, the signal sensor 190 may be implemented as a frequency measuring instrument. According to an embodiment, a change in electrical characteristics in the body of the user may cause a change in electrostatic capacity, and the change in electrostatic capacity may bring about a change in a magnetic oscillation circuit frequency.

According to an embodiment, the controller 120 may receive measurement data in the form of a frequency. The controller 120 may convert the data in the form of a frequency into an impedance signal. According to an embodiment, the controller 120 may control the signal sensor 190 to operate as a frequency measuring device.

As illustrated in FIG. 3B, the controller 120 may control a switching device 126 for current connection between the signal source 170 and the probe 180. According to an embodiment, an AC signal transmitted from the impedance sensor 111 may pass through the body of the user in at least two directions. For example, the at least two directions may include a direction based on muscle fibers and a direction traversing the muscle fibers, but are not limited thereto.

When the AC signal is transmitted in at least two directions, when determining the GI, the wearable apparatus 100 may reflect anisotropic properties of a biological tissue of the user, such that the determined GI may have increased accuracy.

An oscillator 125 is a basic element of the magnetic oscillation circuit. The oscillator 125 may operate by a logic gate or an amplifying element. An oscillation frequency may be set by inductance of inductors L1 or L2, and may be set by a capacitance formed by the probe 180. According to an embodiment, a switching element 251 controlled by the controller 120 may control currents of the inductors L1 and L2 in order to provide two oscillation frequencies.

According to an embodiment, the additional sensors 101 may include a temperature sensor 113, an optical sensor 116, an operation sensor 115, and a heartbeat sensor 117, but are not limited thereto. The temperature sensor 113 may monitor a change in temperature of the body of the user. The optical sensor 116 may monitor a skin characteristic of the user. The operation sensor 115 may monitor physical activity of the user. The heartbeat sensor 117 may monitor the heartbeat of the user based on a predetermined cycle.

According to another embodiment illustrated in FIG. 3C, the signal source 170 may be an AC power supply (for example, a frequency range of 10 kHz to 10 Mhz). The signal sensor 190 may be implemented as an amplitude and phase detector, and the controller 120 may receive amplitude data and phase data with respect to an electrical characteristic generated inside the body of the user. According to an embodiment, the controller 120 may include an analog-to-digital converter (ADC) 121 or an interface configured to receive the amplitude data and the phase data. The controller 120 may convert the received amplitude data and the received phase data into a complex impedance signal.

According to an embodiment, the probe 180 may transmit an AC signal in at least two directions. According to an embodiment, the probe 180 may include tetrapolar circuits.

According to an embodiment, the probe 180 may be implemented as two forms of tetrapolar circuits. For example, the probe 180 may include a tetrapolar circuit arranged based on muscle fibers and a tetrapolar circuit arranged to traverse the muscle fibers. In this case, the probe 190 may obtain a large electrical characteristic difference from the body of the user, due to anisotropic properties of a biological tissue.

According to an embodiment, the signal source 170 may output two types of signals including a zero-phase signal and a reverse-phase (180 degrees) signal (a reverse signal). Also, the probe 180 may output the two types of signals via a differential amplifier 127.

The differential amplifier 127 may reduce intervention signals from a power line (50 Hz/60 Hz) and other sources.

According to an embodiment, the probe 180 may be implemented as a non-contact structure, which is coupled to the body of the user in a capacitance manner. Also, according to another embodiment, the probe 180 may be implemented as a non-contact structure, which is inductively coupled to the body of the user.

Hereinafter, an operation performed by the wearable apparatus 100 to monitor eating habits of a user by using the impedance sensor 111 will be described in detail, by referring to FIG. 4.

Figure 4:
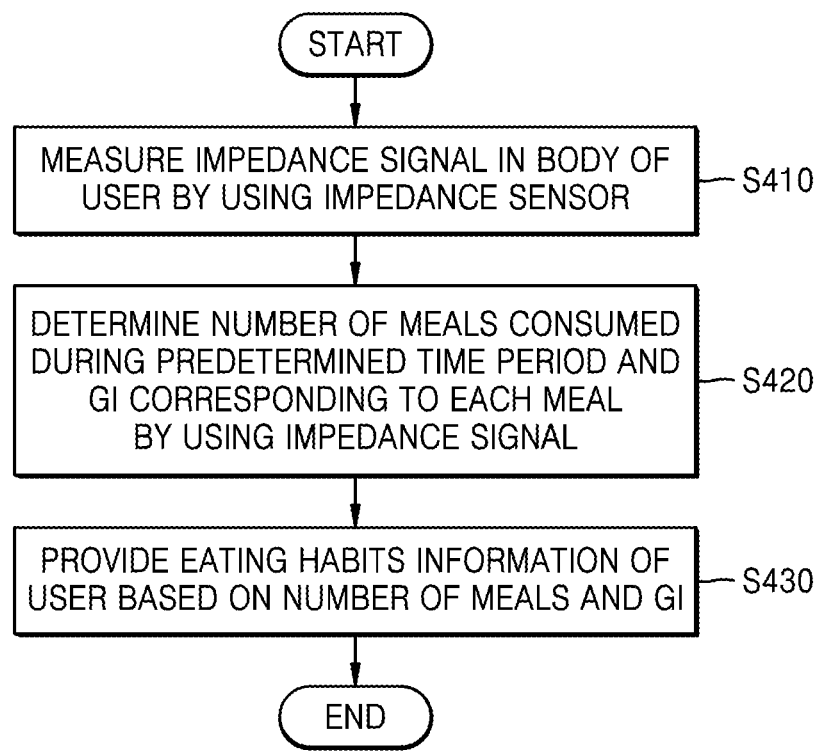
FIG. 4 is a flowchart of a method of providing eating habits information, according to an embodiment.

FIG. 4 is a flowchart of a method of providing eating habits information, according to an embodiment.

In operation S410, according to an embodiment, the wearable apparatus 100 may measure an impedance signal in a body of the user by using the impedance sensor 111. The wearable apparatus 100 may transmit an AC to the body of the user via the impedance sensor 111 and analyze a returning AC to measure a change in an impedance signal in the body.

For example, the wearable apparatus 100 may measure a frequency-dependent impedance, when a current having low amplitude is applied to a biological tissue. At a low frequency of about 1 kHz, in a cell membrane having a characteristic of a capacitor in the body of the user, a current may flow via an extracellular liquid. However, at a high frequency, a current may be induced in the cell membrane and an intracellular liquid. At a high frequency range, the current may flow via the extracellular liquid based on the Ohm method, and the current may flow via the cell membrane and the extracellular liquid based on a capacitor method. An AC resistance hereby generated and measurable has an Ohmic resistance (R) and a capacitive reactance (Xc), and thus, may be referred to as bioelectrical impedance Z. That is, the wearable apparatus 100 may measure the change in impedance signal based on the fact that an impedance of the body of the user has different conductivities in the body.

According to an embodiment, the probe 180 of the impedance sensor 111 may transmit an AC signal in at least two directions by taking into account an anisotropic characteristic of a muscle tissue. For example, the probe 180 may transmit the AC signal in a first direction based on muscle fibers and a second direction traversing the muscle fibers.

In operation S420, according to an embodiment, the wearable apparatus 100 may determine the number of meals consumed during a predetermined time period and a GI corresponding to each meal, by using the impedance signal.

According to an embodiment, the wearable apparatus 100 may sense a change in blood sugar levels in the body of the user, by sensing a change in the impedance signal. This may be possible since the change in blood sugar levels in the body of the user may cause a change in potassium and sodium ion concentrations in the blood, and the change in potassium and sodium ion concentrations in the blood may bring about a change in a bioimpedance spectrum in the blood.

According to an embodiment, the wearable apparatus 100 may determine the GI corresponding to each meal by analyzing the change in blood sugar levels in the body of the user. For example, the wearable apparatus 100 may generate a blood sugar curve by using the impedance signal and analyze the generated blood sugar curve to determine the GI corresponding to each meal. Here, the wearable apparatus 100 may generate or analyze the blood sugar curve based on machine learning.

When the blood sugar curve dramatically rises and then dramatically falls, the GI corresponding to the meal may be high. On the contrary, when the blood sugar curve gradually rises and then gradually falls, the GI corresponding to the meal may be low. An operation performed by the wearable apparatus 100 to analyze the blood sugar curve will be described in detail below by referring to FIG. 5.

According to an embodiment, the wearable apparatus 100 may obtain additional data which affects blood sugar in addition to consumption of food, and may correct the determined GI based on the additional data. For example, the wearable apparatus 100 may correct the GI by taking into account body temperature information, sweating amount information, skin characteristics information, heartbeat information, blood pressure information, activity information, etc. of the user. Alternatively, the wearable apparatus 100 may correct the GI by using metabolic characteristics information of the user. An operation performed by the wearable apparatus 100 to correct the GI will be described in detail below by referring to FIGS. 10 and 11.

The number of meals may be determined based on how many times the user has a meal during a predetermined time period. The predetermined time period may be a day, a week, a month, etc., but is not limited thereto. The predetermined time period may be altered by the user or a system.

According to an embodiment, the wearable apparatus 100 may determine the number of meals consumed by the user, based on a point in time when the impedance signal steeply increases during the predetermined time period. Alternatively, the wearable apparatus 100 may determine the number of meals that the user has consumed during the predetermined time period, based on a point in time when the blood sugar increases in the blood sugar curve. For example, when the predetermined time period is a day, the wearable apparatus 100 may determine the number of meals and the number of snacks during a day as "5 times."

In operation S430, the wearable apparatus 100 may provide the eating habits information of the user based on the number of meals and the GI, according to the embodiment.

According to an embodiment, the eating habits information may include the number of meals, the number of snacks, eating times, an average eating duration time, the blood sugar curve, information of the GI corresponding to each meal (for example, a numerical value, a graph, low/mid/high), a glucose tolerance (GL), information of a level of risk of eating habits, etc., but is not limited thereto.

According to an embodiment, the wearable apparatus 100 may generate the eating habits information of the user by comparing a GI graph (or a blood sugar curve) with a predetermined GI graph (or a predetermined blood sugar curve). For example, when the GI graph with respect to the user is substantially the same as the GI graph with respect to a healthy group, the wearable apparatus 100 may generate information to advise the user to maintain current eating habits. On the contrary, when the GI graph with respect to the user is substantially the same as the GI graph with respect to an unhealthy group, the wearable apparatus 100 may generate information indicating the risk of current eating habits.

According to an embodiment, the wearable apparatus 100 may output the eating habits information of the user via an output unit (for example, a display, a speaker, etc.) of the wearable apparatus 100. For example, the wearable apparatus 100 may output the eating habits information of the user as an image (a still image, a video, etc.), a sound signal, a vibration signal, etc. However, the present disclosure is not limited thereto.

According to an embodiment, the wearable apparatus 100 may output the eating habits information of the user via an external apparatus (for example, a mobile phone). An operation performed by the wearable apparatus 100 to output the eating habits information of the user via the external apparatus will be described in detail below by referring to FIGS. 14 through 16.

According to an embodiment, the wearable apparatus 100 may output at least one of information about recommendations for improving eating habits, information about exercise recommendations, and information about prediction of a body-shape change based on eating habits improvement, based on the eating habits information of the user. Also, the wearable apparatus 100 may recommend an application based on the eating habits information of the user. For example, the wearable apparatus 100 may recommend a weight management application, a diet application, an exercise management application, a disease management application, etc., based on the eating habits information of the user.

Figure 5:
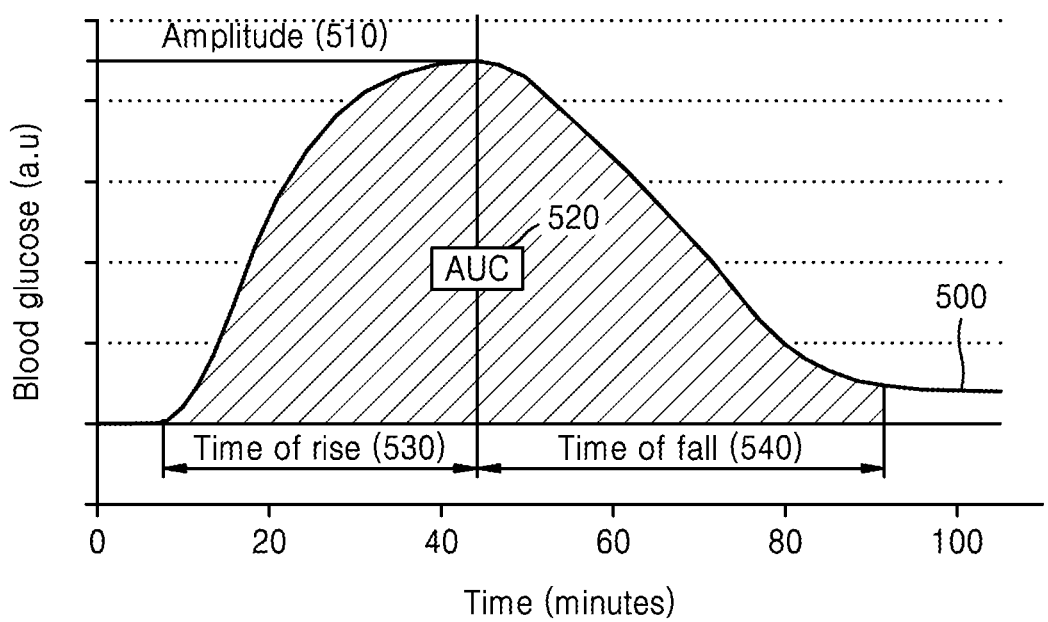
FIG. 5 is a graph for describing a change in blood sugar levels after consumption of food, according to an embodiment.

FIG. 5 is a graph for describing a change in GI after consumption of food, according to an embodiment.

According to an embodiment, the wearable apparatus 100 may transmit an appropriate AC (for example, 10 to 100 kHz) to a body of a user by using at least two electrodes, and then, may measure a voltage. According to an embodiment, the wearable apparatus 100 may detect a change in blood sugar according to time by analyzing an impedance spectrum with respect to the voltage. According to an embodiment, the wearable apparatus 100 may generate the change in blood sugar according to time as a graph (hereinafter, a blood sugar curve 500).

According to an embodiment, the wearable apparatus 100 may determine a GI corresponding to each meal by analyzing the blood sugar curve 500. According to an embodiment, the wearable apparatus 100 may calculate the GI corresponding to each meal by analyzing an area under the curve (AUC). For example, the GI may be calculated by comparing an AUC during two hours after consumption of a glucose liquid solution with an AUC after consumption of a corresponding meal.

The GI=(the AUC after meal/the AUC after consumption of the glucose liquid solution)×100

Referring to FIG. 5, the wearable apparatus 100 may identify that amplitude of the blood sugar curve 500 rises (530) after a change in an impedance signal in the body of the user is sensed, and after about forty (40) minutes, the blood sugar curve 500 reaches the maximum amplitude 510. Also, the wearable apparatus 100 may identify that the amplitude of the blood sugar curve 500 falls according to time after about 40 minutes. When the amplitude of the blood sugar curve 500 falls, the wearable apparatus 100 may determine that the user has finished a meal.

Hereinafter, an operation performed by the wearable apparatus 100 to calculate the number of meals consumed by a user and a GI corresponding to each meal will be described by referring to FIG. 6.

Figure 6:
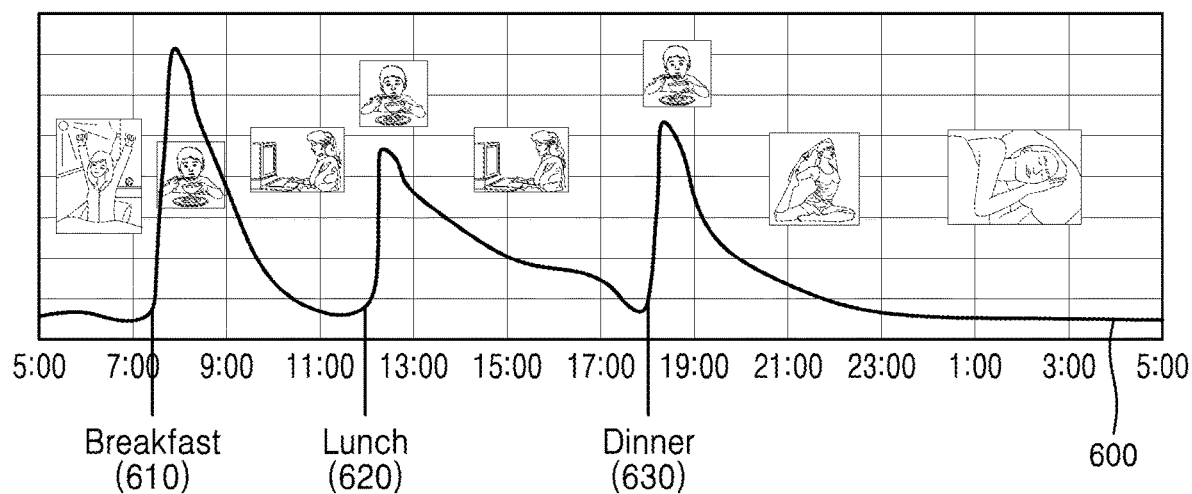
FIG. 6 is a graph for analyzing a blood sugar curve generated based on time in which a user consumes food during a day, according to an embodiment.
Figure 6:
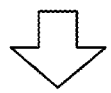

FIG. 6 is a graph for analyzing a blood sugar curve 600 generated according to time in which a user consumes food during a day, according to an embodiment. In FIG. 6, a case in which the user wearing the wearable apparatus 100 has breakfast at 7:30 am, lunch at 12 pm, and dinner at 6 pm will be described as an example. Referring to FIG. 6, the wearable apparatus 100 may generate the blood sugar curve 600 of the user, by using an impedance signal sensed from the user. Since the user has the meals at 7:30 am (610), at noon (620), and at 6 pm (630), the wearable apparatus 100 may generate the blood sugar curve 600, whereby the blood sugar increases at 7:30 am (610), at noon (620), and at 6 pm (630).

Also, the wearable apparatus 100 may determine the number of meals during a predetermined time period and the GI corresponding to each meal, by analyzing the blood sugar curve 600. For example, the wearable apparatus 100 may identify that the user had a meal three times per day, since the blood sugar rose in the blood sugar curve 600 at around 7:30 am (610), noon (620), and 6 pm (630). Also, the wearable apparatus 100 may calculate that the GI corresponding to breakfast is 80, the GI corresponding to lunch is 60, and the GI corresponding to dinner is 55, by analyzing an AUC in the blood sugar curve 600.

Figure 7:
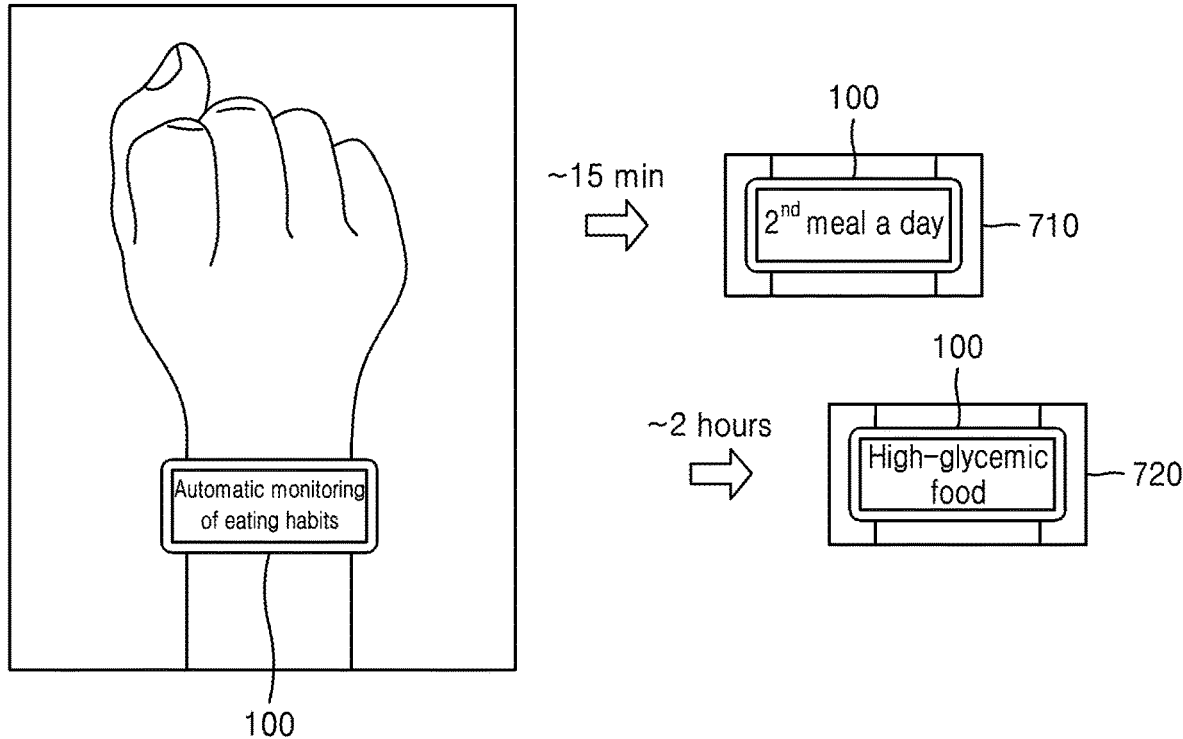
FIG. 7 illustrates an example of providing eating habits information via a wearable apparatus, according to an embodiment.

FIG. 7 illustrates an example of providing eating habits information via the wearable apparatus 100, according to an embodiment.

According to an embodiment, the wearable apparatus 100 may include a display configured to provide the eating habits information to a user. The wearable apparatus 100 may provide the eating habits information to the user via text, an image, a picture, a video, etc., by using the display.

For example, when it is determined that the user is having a second meal (for example, lunch) during a predetermined time period, the wearable apparatus 100 may notify the user that the user is having the second meal. As shown in 710 of FIG. 7, the wearable apparatus 100 may notify that the second meal during a day has been finished. Here, the wearable apparatus 100 may provide a text notification to the user based on a predetermined language.

Also, as shown in 720 of FIG. 7, when, after the user has had a meal (for example, after two (2) hours from the start of a meal), a GI in a body of the user is measured to be higher than a predetermined reference GI, the wearable apparatus 100 may output a notification that a high glycemic food has been consumed.

According to an embodiment, the wearable apparatus 100 may provide the eating habits information to the user by using a sound notification, an alarm sound output, an alarm vibration output, etc. However, the present disclosure is not limited thereto.

Figure 8:
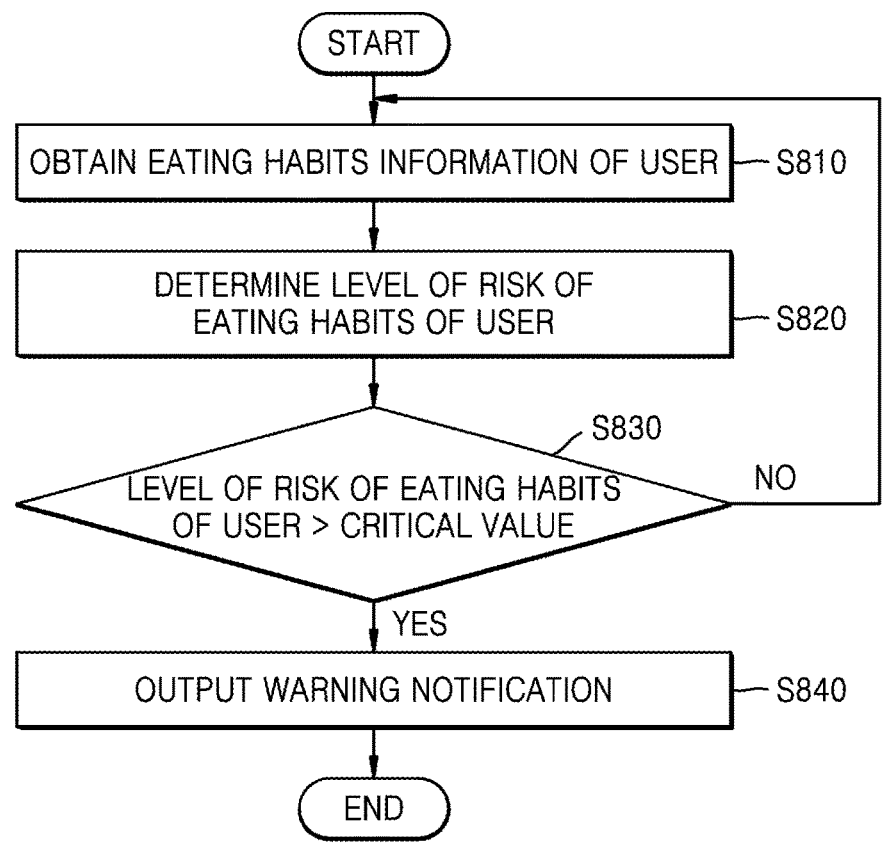
FIG. 8 is a flowchart of a method of outputting a notification based on a level of risk of eating habits of a user, according to an embodiment.

FIG. 8 is a flowchart of a method of outputting a notification based on a level of risk of eating habits of a user, according to an embodiment.

In operation S810, the wearable apparatus 100 may obtain eating habits information of the user, according to an embodiment.

The wearable apparatus 100 may obtain the eating habits information, such as a GI corresponding to each meal, the number of meals consumed by the user, etc., by analyzing an impedance signal. The wearable apparatus 100 may form the eating habits information of the user based on a predetermined method. For example, the wearable apparatus 100 may form the eating habits information of the user by using at least one of an analysis of GIs based on time, an analysis of a difference between a highest GI and a lowest GI, and an average of the number of meals. However, the present disclosure is not limited thereto.

In operation S820, the wearable apparatus 100 may determine the level of risk of eating habits of the user, according to an embodiment.

The wearable apparatus 100 may determine the level of risk of the eating habits of the user based on a predetermined level, by using the eating habits information of the user. For example, the wearable apparatus 100 may determine the level of risk of the eating habits of the user, based on an extent to which the eating habits information of the user deviates from a predetermined regular number of meals (for example, exceeding the number of meals, a fewer number of meals, etc.). Also, the wearable apparatus 100 may determine the level of risk of the eating habits of the user, based on the GI corresponding to each meal of the user. For example, the wearable apparatus 100 may determine the level of risk of the eating habits of the user, based on how much higher a calculated GI is than a predetermined regular GI. However, the present disclosure is not limited thereto.

According to an embodiment, the wearable apparatus 100 may receive predetermined indices, based on which the level of risk of the eating habits may be determined, from other apparatuses, directly from the user, or from a server via a network.

Alternatively, the wearable apparatus 100 may determine an average number of meals consumed by the user, an average GI, etc. based on the eating habits information of the user, and may select the average number of meals, the average GI (for example, 70), etc., as comparative indices.

In operation S830, the wearable apparatus 100 may compare the determined level of risk of the eating habits of the user with a predetermined critical value, according to an embodiment.

According to an embodiment, when the determined level of risk of the eating habits of the user is greater than the predetermined critical value, the wearable apparatus 100 may determine that the eating habits of the user are dangerous. For example, when the number of meals consumed by the user per day is equal to or less than one (1), or greater than seven (7), the wearable apparatus 100 may determine that the eating habits of the user are risky. Also, when a GI corresponding to a meal consumed after 10 pm is greater than 90, the wearable apparatus 100 may determine that the eating habits of the user are dangerous.

Also, when the level of risk of the eating habits of the user is less than the predetermined critical value, the wearable apparatus 100 may repeatedly perform the operation of obtaining the eating habits information of the user.

In operation S840, when it is determined that the level of risk of the eating habits of the user is greater than the predetermined critical value, the wearable apparatus 100 may output a warning notification, according to an embodiment.

According to an embodiment, the wearable apparatus 100 may output the warning notification as a predetermined warning notification. The wearable apparatus 100 may notify the user of how high the level of risk of the eating habits of the user is, based on the number of warning notifications. Alternatively, the wearable apparatus 100 may output the level of risk of the eating habits of the user via a pre-recorded voice recording. Alternatively, the wearable apparatus 100 may output the level of risk of the eating habits of the user by using at least one of a visual method and a haptic method, in addition to the audio method. However, the present disclosure is not limited thereto.

Figure 9:
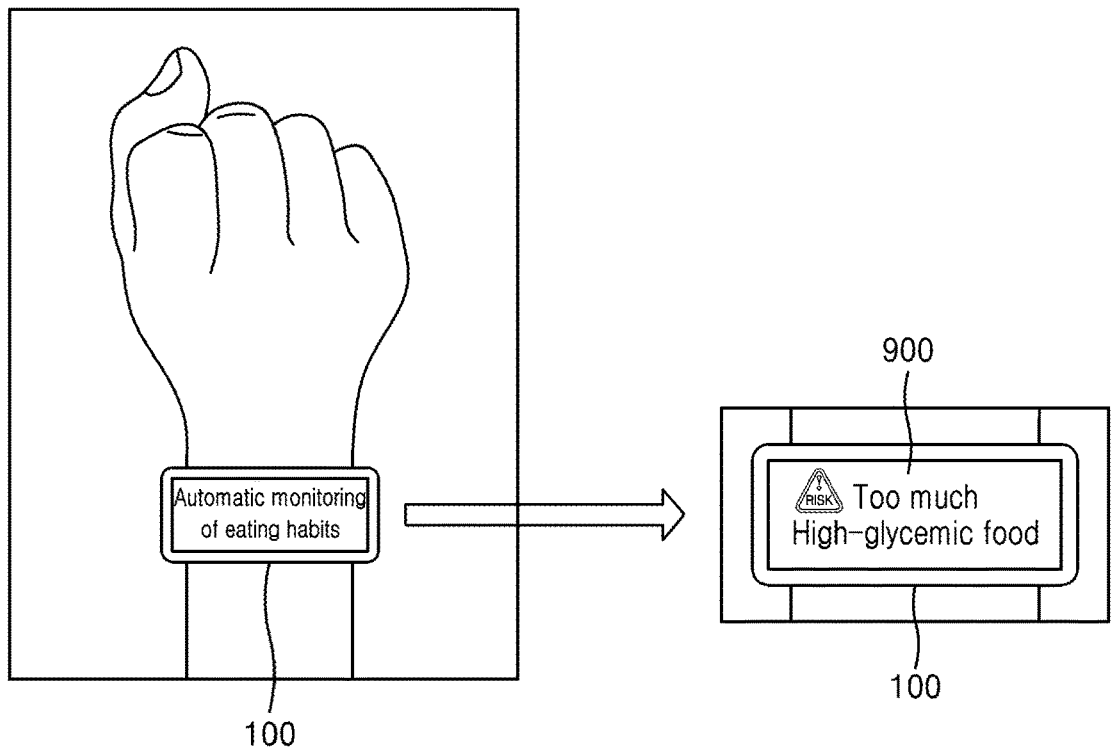
FIG. 9 is a view for describing an example of a wearable apparatus configured to warn against a level of risk of eating habits of a user, according to an embodiment.

FIG. 9 illustrates the wearable apparatus 100 configured to warn of a level of risk of eating habits of a user, according to an example embodiment.

Referring to FIG. 9, the wearable apparatus 100 may determine the level of risk of the eating habits of the user and may warn of the level of risk of the eating habits of the user via a display. For example, when the number of times in a day that a post-meal GI exceeds a critical value is equal to or greater than two (2), the wearable apparatus 100 may determine that the level of risk of the eating habits of the user is high. In this case, the wearable apparatus 100 may notify the user that the user is having a meal of a high GI. For example, the wearable apparatus 100 may output alarm text 900, such as "too much high-glycemic food."

Also, the wearable apparatus 100 may warn of the level of risk of the eating habits of the user by using video, audio, an alarm sound, alarm vibration, etc.

Figure 10:
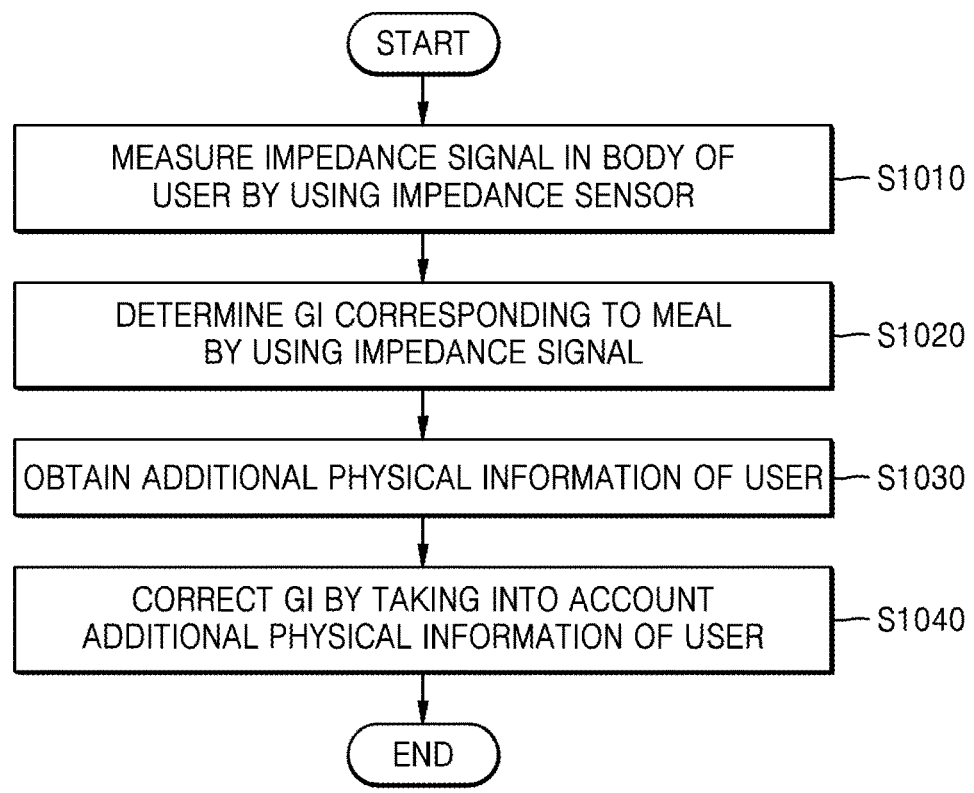
FIG. 10 is a flowchart of a process of correcting a GI with respect to a user by using additional physical information of the user, according to an embodiment.

FIG. 10 is a flowchart of a process of correcting a GI with respect to a user by using additional physical information of the user, according to an embodiment.

In operation S1010, according to an embodiment, the wearable apparatus 100 may measure an impedance signal in a body of the user by using the impedance sensor 111. Operation S1010 corresponds to operation S410 of FIG. 4, and thus, its detailed description will be omitted.

In operation S1020, according to an embodiment, the wearable apparatus 100 may determine a GI corresponding to a meal by using the impedance signal. Operation S1020 corresponds to operation S420 of FIG. 4, and thus, its detailed description will be omitted.

In operation S1030, according to an embodiment, the wearable apparatus 100 may obtain additional physical information of the user. Here, the additional physical information may include, but is not limited to, body temperature information, sweating amount information, skin characteristics information, heartbeat information, blood pressure information, activity information, etc. of the user.

According to an embodiment, the wearable apparatus 100 may obtain the additional physical information of the user by using at least one of a temperature sensor configured to measure a body temperature of a user, a humidity sensor configured to measure an amount of sweating of a user, a reflective optical sensor configured to measure a skin characteristic of a user, a heartbeat sensor configured to measure the heartbeat of a user, a blood pressure sensor configured to measure a blood pressure of a user, and an operation sensor configured to measure activity of a user.

Also, the wearable apparatus 100 may obtain external environment information of the wearable apparatus 100 via other sensors of the wearable apparatus 100. For example, the wearable apparatus 100 may obtain external environment information such as an external temperature, humidity, noise, etc.

In operation S1040, according to an embodiment, the wearable apparatus 100 may correct the determined GI by taking into account the additional physical information of the user.

The wearable apparatus 100 may correct the determined GI by taking into account at least one of body temperature information, sweating amount information, skin characteristics information, heartbeat information, blood pressure information, and activity information of the user.

For example, when physical information different from regular physical information of the user is obtained, the wearable apparatus 100 may correct the GI by taking into account the different physical information. In more detail, when the wearable apparatus 100 obtains information indicating that the body temperature of the user is increasing, the amount of sweating is increasing, the skin is moistening, and the heartbeat is increasing, as the user wearing the wearable apparatus 100 is performing an exercise, the wearable apparatus 100 may correct the GI by taking into account the fact that a blood sugar level of the user may be higher or lower than a regular blood sugar level of the user.

Meanwhile, correcting the GI may include correcting an impedance signal or correcting a blood sugar curve.

According to an embodiment, the wearable apparatus 100 may generate eating habits information of the user by using the corrected GI.

Figure 11:
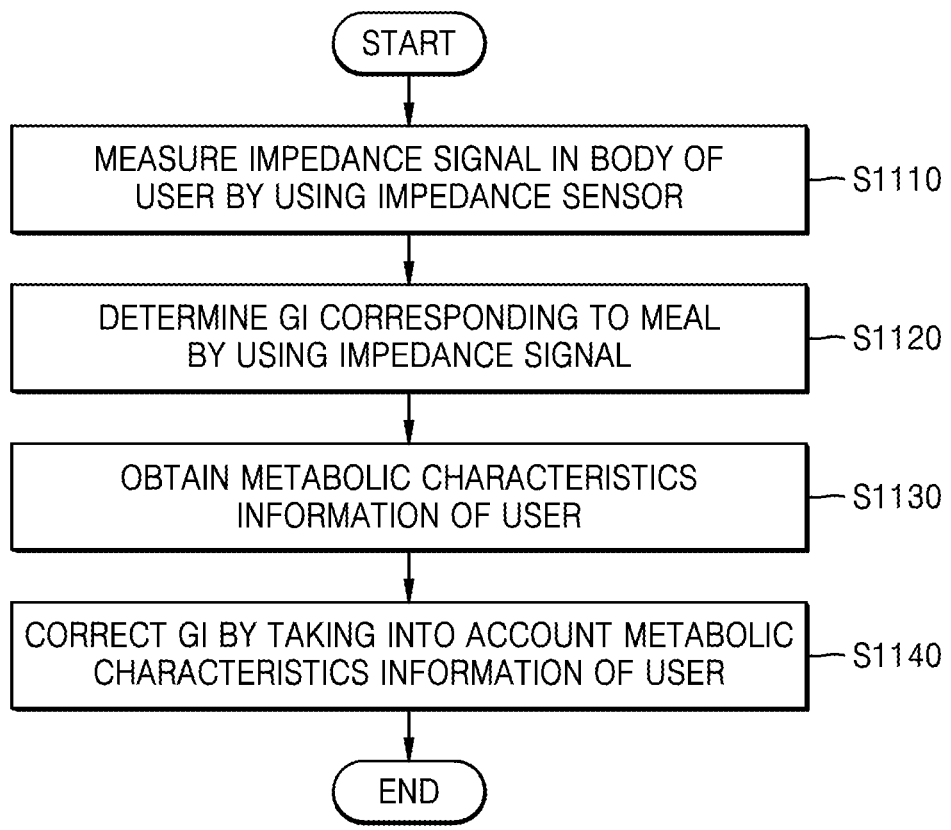
FIG. 11 is a flowchart of a process of correcting a GI with respect to a user by using metabolic characteristics information of the user, according to an embodiment.

FIG. 11 is a flowchart of a process of correcting a GI by using metabolic characteristics information of a user, according to an embodiment.

In operation S1110, according to an embodiment, the wearable apparatus 100 may measure an impedance signal in the body of the user by using the impedance sensor 111. Operation S1110 corresponds to operation S410 of FIG. 4, and thus, its detailed description will be omitted.

In operation S1120, according to an embodiment, the wearable apparatus 100 may determine a GI corresponding to a meal, by using the impedance signal. Operation S1120 corresponds to operation S420 of FIG. 4, and thus, its detailed description will be omitted.

In operation S1130, according to an embodiment, the wearable apparatus 100 may obtain the metabolic characteristics information of the user. The metabolic characteristics information may denote characteristics with respect to a decomposition (digestion) capacity of an individual with respect to a specific food, and the metabolic characteristics may vary based on an individual physical ability.

According to an embodiment, the wearable apparatus 100 may directly generate the metabolic characteristics information of the user. An operation performed by the wearable apparatus 100 to directly generate the metabolic characteristics information of the user will be described in detail below by referring to FIG. 12.

According to an embodiment, the wearable apparatus 100 may receive the metabolic characteristics information from the user. Also, the wearable apparatus 100 may download the metabolic characteristics information of the user from an individual server of the user outside the wearable apparatus 100. However, the present disclosure is not limited thereto.

In operation S1140, according to an embodiment, the wearable apparatus 100 may correct the GI by using the metabolic characteristics information of the user.

According to an embodiment, the wearable apparatus 100 may correct the GI corresponding to each meal, by correcting an impedance signal or a blood sugar curve by using the metabolic characteristics information of the user.

According to an embodiment, the wearable apparatus 100 may generate eating habits information of the user by using the corrected GI.

Hereinafter, an operation performed by the wearable apparatus 100 to directly generate the metabolic characteristics information of the user will be described by referring to FIG. 12.

Figure 12:
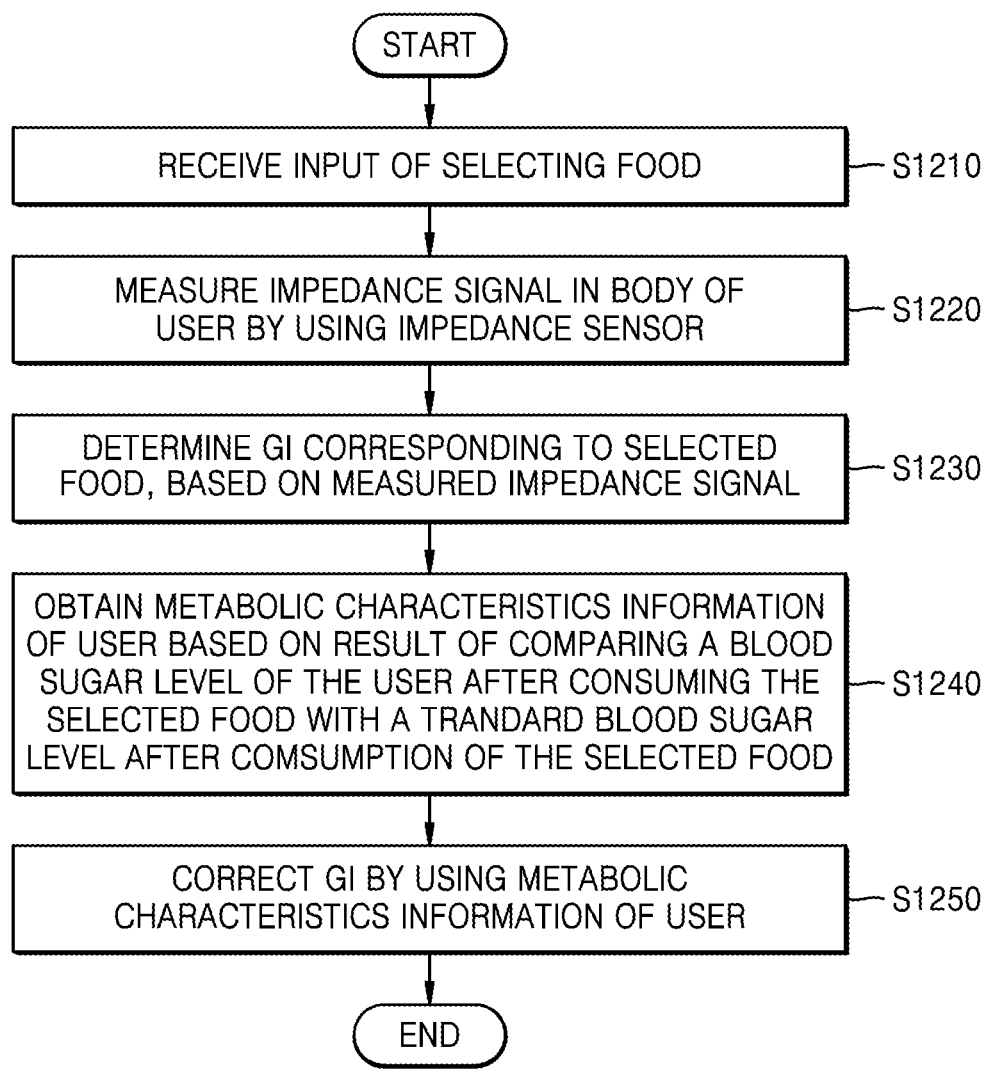
FIG. 12 is a flowchart of a process of correcting a GI with respect to a user by using metabolic characteristics information of the user, according to an embodiment.

FIG. 12 is a flowchart of a process of correcting a GI by using the metabolic characteristics information of the user, according to an embodiment.

In operation S1210, according to an embodiment, the wearable apparatus 100 may receive a user input of selecting food to be consumed. For example, the wearable apparatus 100 may directly receive a name of the food from the user. Also, the wearable apparatus 100 may provide a predetermined food list and receive an input of selecting a food from the predetermined food list.

In operation S1220, according to an embodiment, the wearable apparatus 100 may measure an impedance signal in a body of the user.

When the impedance signal changes, the wearable apparatus 100 may determine that the user has consumed the selected food. The wearable apparatus 100 may generate a blood sugar curve by using the impedance signal.

In operation S1230, according to an embodiment, the wearable apparatus 100 may determine a GI corresponding to the selected food based on the measured impedance signal. For example, the wearable apparatus 100 may determine the GI of the food selected by the user by analyzing the blood sugar curve generated based on the impedance signal.

In operation S1240, according to an embodiment, the wearable apparatus 100 may obtain the metabolic characteristics information of the user, based on a result of comparing a blood sugar level of the user after consuming the selected food with a standard blood sugar level after consumption of the selected food.

For example, the wearable apparatus 100 may generate the metabolic characteristics information of the user based on a difference between the blood sugar level of the user having consumed the selected food and the standard blood sugar level after consumption of the selected food.

In operation S1250, according to an embodiment, the wearable apparatus 100 may correct the GI corresponding to each meal by using the metabolic characteristics information of the user.

According to an embodiment, the wearable apparatus 100 may obtain, a plurality of times, a blood sugar level of the user having consumed a specific food selected by the user. Also, the wearable apparatus 100 may measure the blood sugar level of the user having consumed the specific food, based on a predetermined time period. The wearable apparatus 100 may generate the metabolic characteristics information of the user by using a difference between the blood sugar level of the user having consumed the specific food and the standard blood sugar level of the specific food, and based on the generated metabolic characteristics information of the user, may generate a corrected GI. The wearable apparatus 100 may correct a GI of another meal consumed by the user at a different time, based on the corrected GI.

Figure 13:
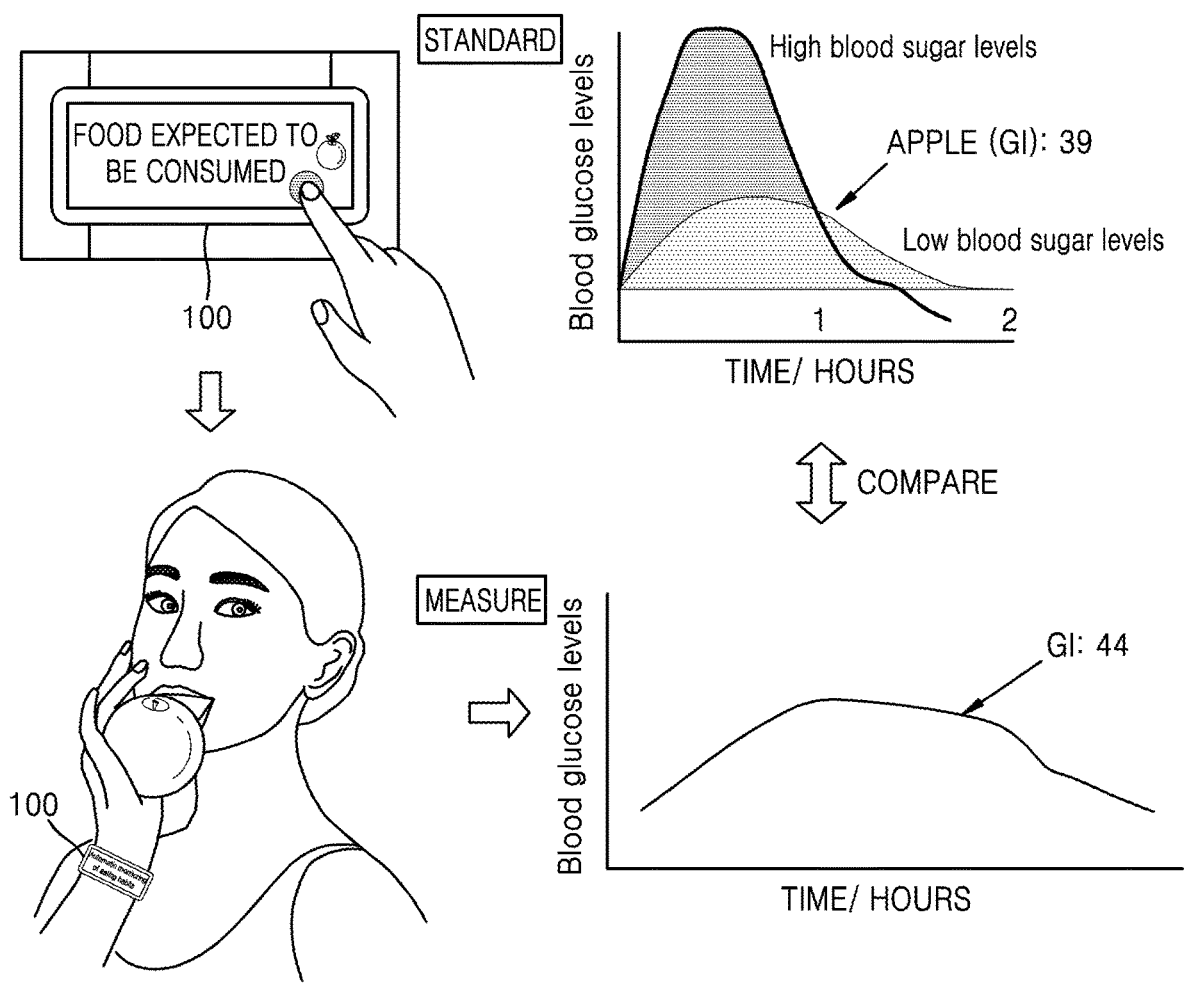
FIG. 13 is a view for describing an example of obtaining metabolic characteristics information, according to an embodiment.

FIG. 13 is a view for describing an example of obtaining metabolic characteristics information, according to an embodiment.

Referring to FIG. 13, the wearable apparatus 100 may include a user input unit configured to receive, from a user, an input of selecting food to be consumed (for example, an apple).

According to an embodiment, the wearable apparatus 100 may further receive identification information, physical state information, etc., of the user, in addition to the input of selecting the food to be consumed, via the user input unit. However, the present disclosure is not limited thereto. Also, the wearable apparatus 100 may receive the input of selecting the food to be consumed, via a touch input, a text input, a video recording, a voice input, etc. However, the present disclosure is not limited thereto.

When an impedance signal in a body of the user changes, the wearable apparatus 100 may determine that the user is eating the apple. In this case, the wearable apparatus 100 may generate a blood sugar curve based on the impedance signal and analyze the blood sugar curve to determine a GI of the apple. For example, the wearable apparatus 100 may determine the GI of the apple as "44," based on a result of analyzing the blood sugar curve.

Also, the wearable apparatus 100 may obtain the metabolic characteristics information of the user, based on a result of comparing a blood sugar level of the user after consuming the apple with a standard blood sugar level of the apple. For example, the wearable apparatus 100 may obtain the metabolic characteristics information of the user by linking the insulin secretion of the user with the metabolic characteristics, based on the comparison of the standard blood sugar level with a measured blood sugar level. The wearable apparatus 100 may correct a GI to be measured later, by reflecting the metabolic characteristics of the user.

Figure 14:
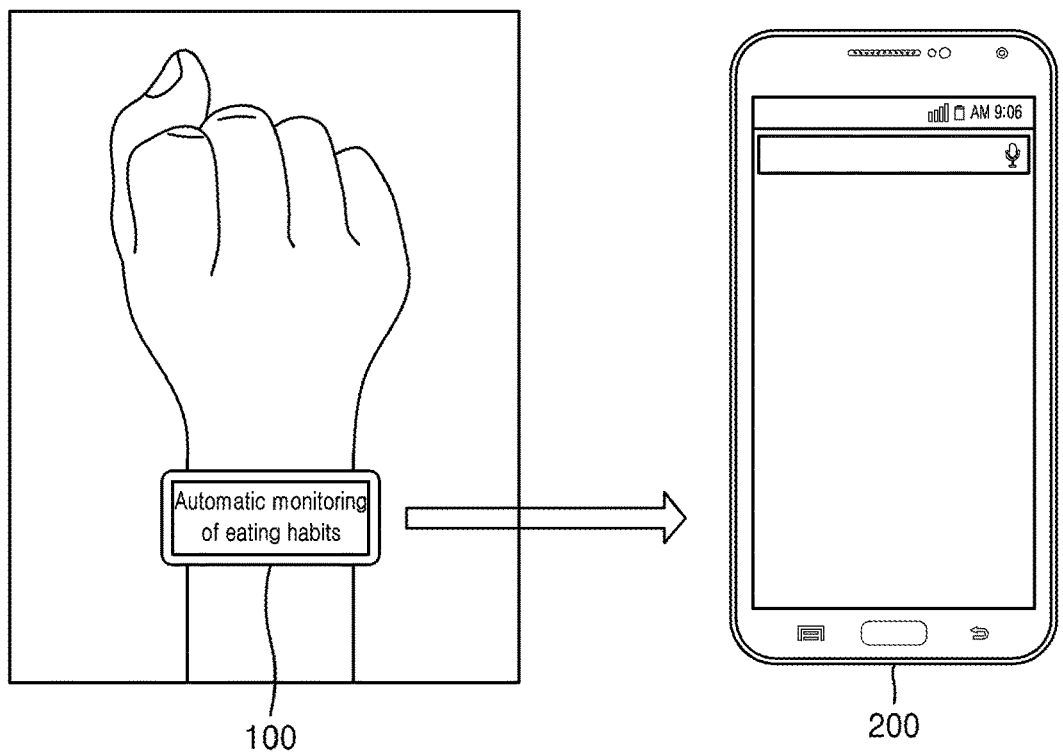
FIG. 14 is a view for describing a system in which a wearable apparatus and an external apparatus are connected to provide eating habits information, according to an embodiment.

FIG. 14 is a view for describing a system in which the wearable apparatus 10 and the external apparatus 200 are connected to provide eating habits information, according to an embodiment.

According to an embodiment, the wearable apparatus 100 may transmit and receive data to and from the external apparatus 200 belonging to a user. The wearable apparatus 100 may transmit, to the external apparatus 200, at least one of eating habits information of the user, a GI, a level of risk of eating habits, the number of meals, and a warning notification based on a determined level of risk of the eating habits.

Here, the external apparatus 200 may include a cellular phone, a smartphone, a notebook computer, a digital broadcasting terminal, a personal digital assistant (PDA), a portable multimedia player (PMP), a camera, a navigation system, a tablet computer, an electronic book (e-book) terminal, a smart watch, etc. However, the present disclosure is not limited thereto. According to an embodiment, the external apparatus 200 may be a device owned by the user, or a device owned by another user. The external apparatus 200 may include a cloud server, a personalized server, or a medical institution server.

The wearable apparatus 200 may be connected with the external apparatus 200 to perform communication with the external apparatus 200. For example, the wearable apparatus 100 may form a short-range communication link with the external apparatus 200 and may form a mobile communication link (for example, 3G, 4G, 5G, etc.) with the external apparatus 200. The short-range communication link may include, but is not limited to, Bluetooth, Bluetooth low energy (BLE), Wifi direct, ultra wideband (UWB), Zigbee, a near-field communication (NFC) unit, Ant+, etc.

The wearable apparatus 100 may perform real-time communication with the external apparatus 200. The wearable apparatus 100 may communicate with the external apparatus 200 based on a predetermined cycle. However, the present disclosure is not limited thereto.

The wearable apparatus 100 may transmit, to the external apparatus 200, all eating habits information obtained by the wearable apparatus 100. Alternatively, the wearable apparatus 100 may transmit only predetermined information to the external apparatus 200. For example, the wearable apparatus 100 may transmit information about the number of meals to the external apparatus 200, only when the number of meals consumed by the user exceeds a predetermined value.

Figure 15:
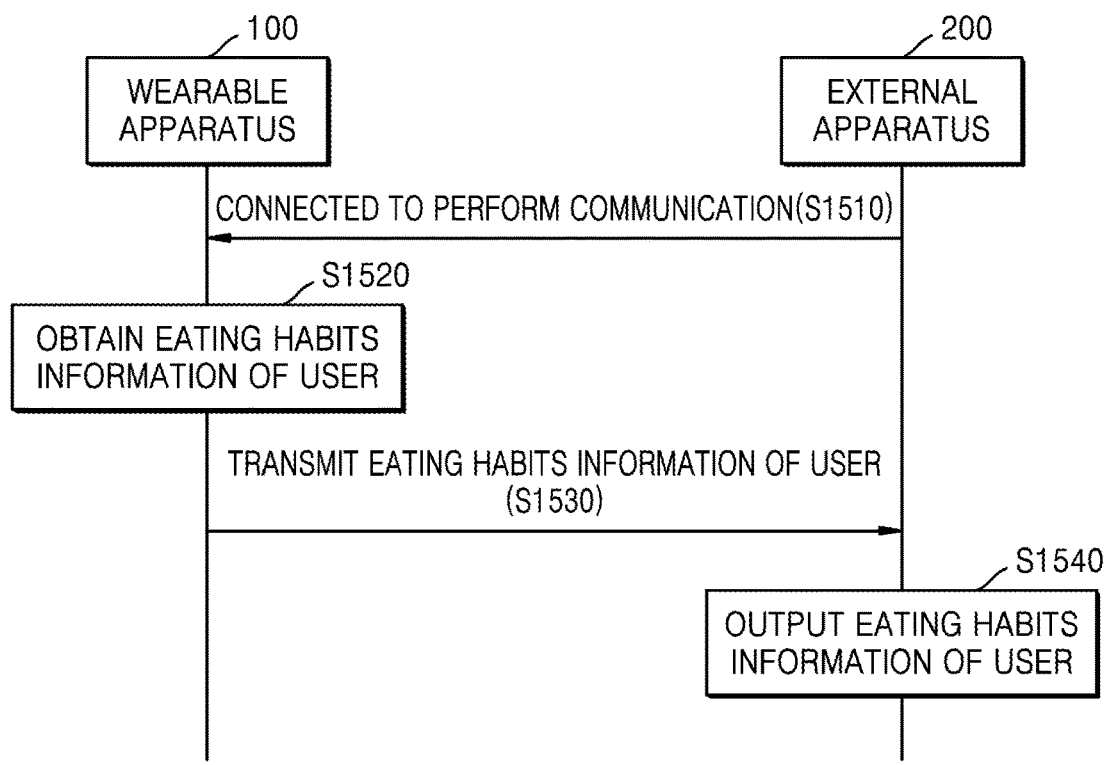
FIG. 15 is a flowchart of a process of exchanging eating habits information between a wearable apparatus and an external apparatus, according to an embodiment.

FIG. 15 is a flowchart of a process of exchanging eating habits information between the wearable apparatus 100 and the external apparatus 200, according to an embodiment.

According to an embodiment, in operation S1510, the wearable apparatus 100 may be connected with the external apparatus 200 to perform communication with the external apparatus 200. According to an embodiment, the wearable apparatus 100 may include a communication unit which may be connected with the external apparatus 20 wirelessly or via wires.

In operation S1520, the wearable apparatus 100 may obtain the eating habits information of the user. As described above, the wearable apparatus 100 may obtain the eating habits information of the user by continually sensing an impedance signal of the user. Operation S1520 corresponds to operation S801, and thus, its detailed description will be omitted.

In operation S1530, the wearable apparatus 100 may transmit the eating habits information of the user to the external apparatus 200. That is, the wearable apparatus 100 may generate the eating habits information of the user, and then, may transmit the generated eating habits information of the user to the external apparatus 200.

In operation S1540, the external apparatus 200 may output the eating habits information of the user. According to an embodiment, the external apparatus 200 may output the eating habits information of the user via visual, auditory, or haptic notification. For example, when the external apparatus 200 is a smartphone of the user, the external apparatus 200 may output the eating habits information of the user via a word, an image, a figure, a video, or the like, by using a display.

Thus, the user may identify his or her eating habits information via the external apparatus 200 and store the eating habits information in the external apparatus 200.

Meanwhile, according to an embodiment, the wearable apparatus 100 may share the eating habits information of the user with an apparatus of a third party. For example, the wearable apparatus 100 may transmit the eating habits information of the user to a mobile terminal of a family member of the user, a server of a medical institution, or a personal health management server.

Figure 16:
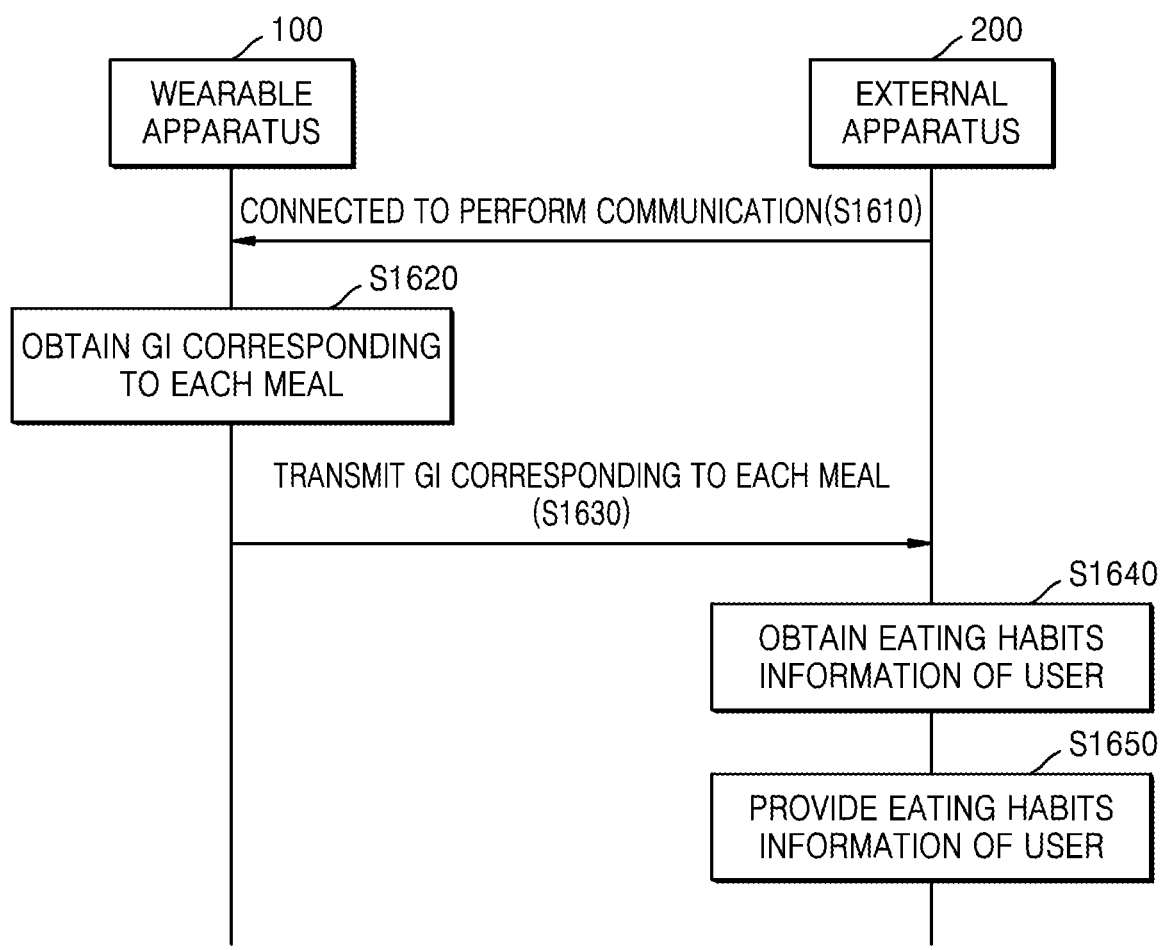
FIG. 16 is a flowchart of a process of providing eating habits information via an external apparatus, wherein the external apparatus receives a GI from a wearable apparatus, according to an embodiment.

FIG. 16 is a flowchart of a process of providing eating habits information via the external apparatus 200 that has received a GI with respect to a user from the wearable apparatus 100, according to an embodiment.

According to an embodiment, in operation S1610, the wearable apparatus 100 may be connected to the external apparatus 200 to perform communication with the external apparatus 200. According to an embodiment, the wearable apparatus 100 may include a communication unit which may be connected with the external apparatus 200 wirelessly or via wires.

According to an embodiment, in operation S1620, the wearable apparatus 100 may determine a GI corresponding to a meal consumed by the user. According to an embodiment, the wearable apparatus 100 may measure the GI in real time by analyzing an impedance signal. Operation S1620 corresponds to operation S420 of FIG. 4, and thus, its detailed description will be omitted.

According to an embodiment, in operation S1630, the wearable apparatus 100 may transmit, to the external apparatus 200, the determined GI corresponding to each of meals. For example, when a request for the GI is received from the external apparatus 200, the wearable apparatus 100 may transmit information of the GI corresponding to each meal to the external apparatus 200.

Alternatively, when a specific event occurs, the wearable apparatus 100 may automatically transmit the information of the GI to the external apparatus 200. For example, when a GI which is equal to or greater than a predetermined GI is sensed, the wearable apparatus 100 may transmit the GI to the external apparatus 200. Alternatively, the wearable apparatus 100 may periodically transmit the information of the GI with respect to the user to the external apparatus 200, based on a predetermined cycle.

According to an embodiment, in operation S1640, the external apparatus 200 may obtain the eating habits information of a user. The external apparatus 200 may generate the eating habits information of the user by analyzing the GI corresponding to each meal. For example, the external apparatus 200 may determine whether the GI determined with respect to the user is equal to or higher than a predetermined standard GI. For example, the external apparatus 200 may determine whether the GI corresponding to each meal is high, regular, or low. Also, the external apparatus 200 may calculate the number of times during a predetermined time period, in which the GI determined with respect to the user is higher than the standard GI.

According to an embodiment, the external apparatus 200 may correct the GI received from the wearable apparatus 100, by using information collected by sensors mounted in the external apparatus 200. For example, the external apparatus 200 may correct the GI by taking into account body temperature information, sweating amount information, skin characteristics information, heartbeat information, blood pressure information, activity information, etc. of the user.

Alternatively, the external apparatus 200 may correct the GI by using the metabolic characteristics information of the user.

According to an embodiment, the external apparatus 200 may generate the eating habits information of the user by using a graph, text, a still image, a video, audio, etc.

According to an embodiment, in operation S1650, the external apparatus 200 may provide the eating habits information of the user. According to an embodiment, the external apparatus 200 may provide the eating habits information of the user via a display, a speaker, a vibration module, etc. of the external apparatus 200.

Also, the external apparatus 200 may provide the eating habits information of the user to another apparatus. Also, the external apparatus 200 may transmit the eating habits information of the user to the wearable apparatus 100.

According to an embodiment, the external apparatus 200 may obtain the eating habits information of the user by using the information regarding the GI, the number of meals, etc. obtained by the wearable apparatus 100, and may provide the eating habits information of the user to the user.

Figure 17:
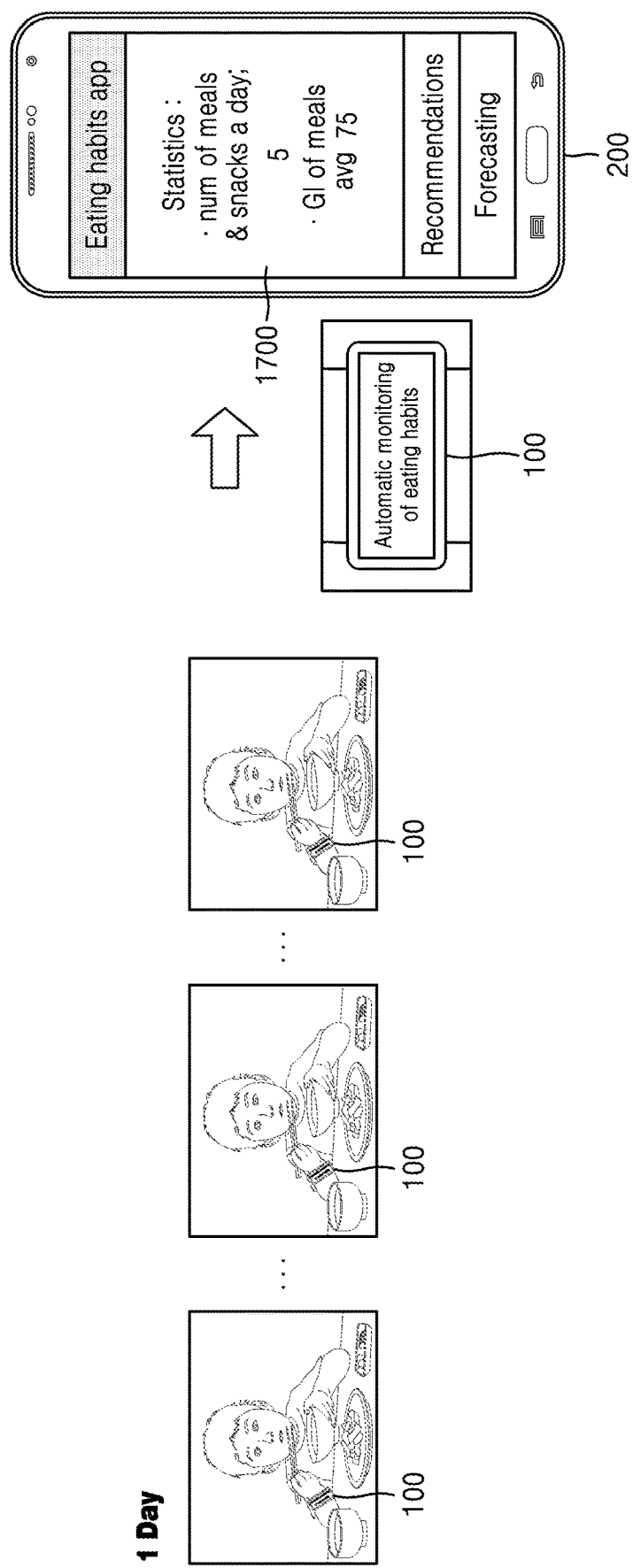
FIG. 17 illustrates a screen, on which an external apparatus provides daily eating habits information of a user, according to an embodiment.

FIG. 17 illustrates a screen, on which the external apparatus 200 provides daily eating habits information 1700 of a user, according to an embodiment. In FIG. 17, a case in which the external apparatus 200 is a mobile phone belonging to the user will be described as an example.

Referring to FIG. 17, the wearable apparatus 100 worn by the user may continually monitor a change in an impedance signal in a body of the user, and may determine the number of meals per day and a GI corresponding to each meal by using the change in the impedance signal. Here, the wearable apparatus 100 or the external apparatus 200 may generate the daily eating habits information 1700 of the user based on the number of meals and the GI corresponding to each meal. Also, the external apparatus 200 may output the daily eating habits information 1700 of the user, via an eating habits management application.

For example, when the blood sugar of the user rises five (5) times during a day, the wearable apparatus 100 may determine that the number of meals (or snacks) per day for the user is 5. In addition, the wearable apparatus 100 may identify that an average GI of the meals is 75. Here, the wearable apparatus 100 may generate the daily eating habits information 1700 of the user based on the number of meals per day and the average GI and may provide the daily eating habits information 1700 to the user via the external apparatus 200.

According to an embodiment, a cycle based on which the wearable apparatus 100 generates eating habits information of the user may be determined based on an input of the user. However, the present disclosure is not limited thereto.

Figure 18:
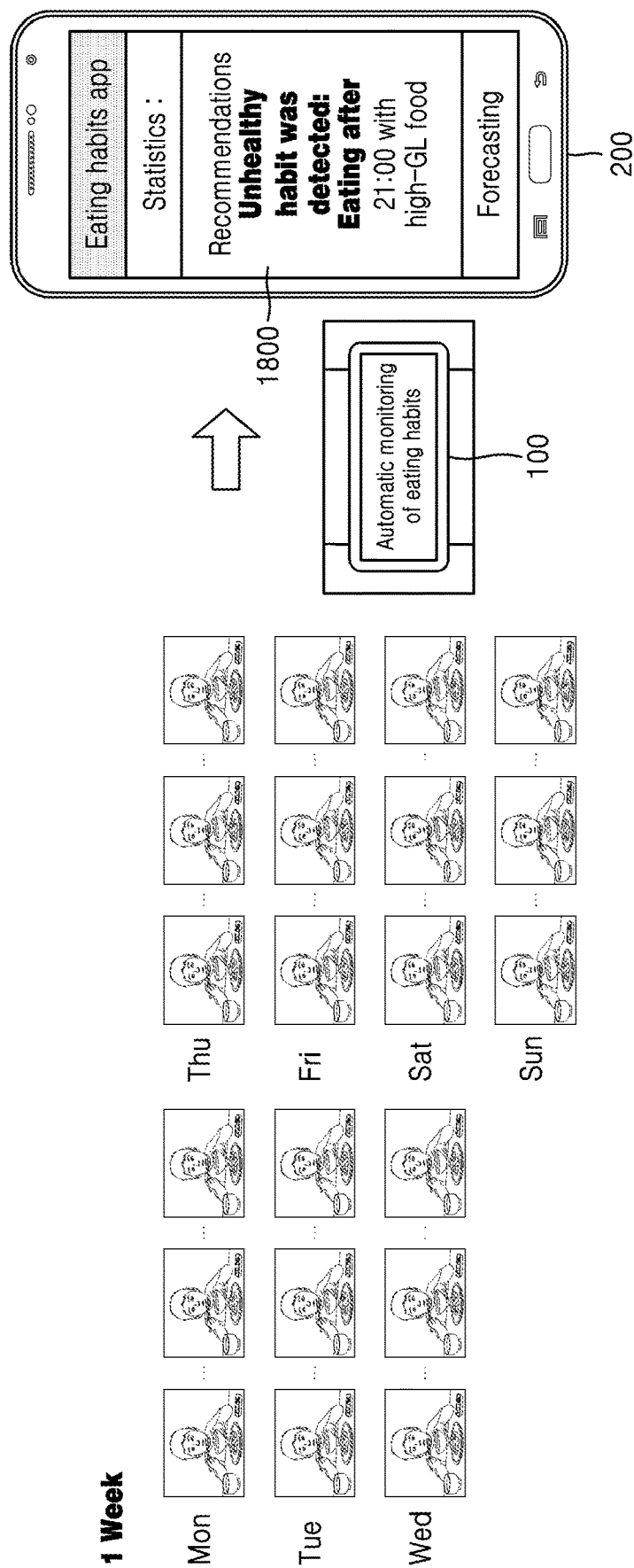
FIG. 18 illustrates a screen, on which an external apparatus provides weekly eating habits information of a user, according to an embodiment.

FIG. 18 illustrates a screen, on which the external apparatus 200 provides weekly eating habits information of a user, according to an embodiment.

Referring to FIG. 18, the wearable apparatus 100 may obtain the weekly eating habits information of the user by checking information about the number of meals per week, information about eating intervals, information about eating times, information about an average eating duration time, information about a blood sugar curve, and information about a GI corresponding to each of meals.

For example, the wearable apparatus 100 may generate the weekly eating habits information of the user by comparing and analyzing daily eating habits information generated with respect to a week.

According to an embodiment, the wearable apparatus 100 may compare the daily eating habits information generated with respect to a week and may determine the daily eating habits information deviating from average eating habits.

Meanwhile, according to an embodiment, the wearable apparatus 100 may analyze the weekly eating habits information of the user and may provide comments with respect to the weekly eating habits information to the user. For example, based on a result of analyzing the weekly eating habits of the user, the wearable apparatus 100 may output, via the external apparatus 200, a message 1800 warning that food having a high GI is consumed after 21:00.

The method of providing the eating habits information illustrated in FIG. 18 is an example, and there may be various methods of analyzing eating habits of a user and determining a level of risk of the eating habits.

Figure 19:
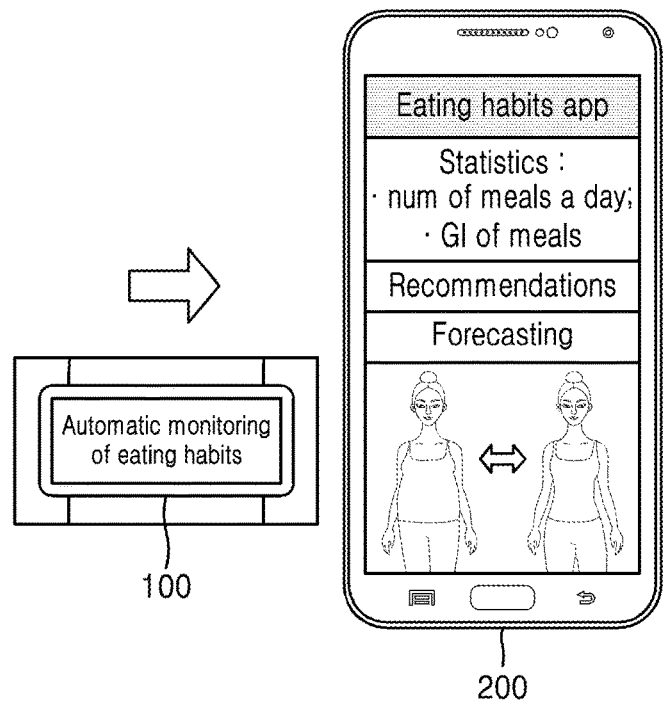
FIG. 19 illustrates a screen, on which an external apparatus provides monthly eating habits information of a user, according to an embodiment.

FIG. 19 illustrates a screen, on which the external apparatus 200 provides monthly eating habits information of a user, according to an embodiment.

According to an embodiment, the wearable apparatus 100 may obtain eating habits information of the user with respect to a month. For example, the wearable apparatus 100 may analyze eating habits of the user per hour, per day, and per week, to obtain the monthly eating habits information of the user.

According to an embodiment, the wearable apparatus 100 may generate the eating habits information of the user by calculating the number of meals consumed by the user per month or an average of GIs. Alternatively, the wearable apparatus 100 may compare the number of meals consumed by the user or the GI with an average critical value, for each day in a month, in order to determine whether there are days in which the number of meals or the GI is equal to or greater than the average critical value. The wearable apparatus 100 may determine a level of risk of the eating habits of the user based on an extent to which the number of meals or the GI of certain days deviates from the average critical value.

The wearable apparatus 100 may transmit the monthly eating habits information of the user to the external apparatus 200, and the external apparatus 200 may output, store, transmit, or additionally analyze the monthly eating habits information of the user.

In FIGS. 17 through 19, the cases in which the wearable apparatus 100 obtains the eating habits information of the user are described as an example. However, the present disclosure is not limited thereto. For example, the wearable apparatus 100 may obtain blood sugar information of the user by using the impedance sensor 111 and may transmit the blood sugar information of the user to the external apparatus 200. Here, the external apparatus 200 may generate daily, weekly, or monthly eating habits information of the user by analyzing the received blood sugar information of the user.

Figure 20:
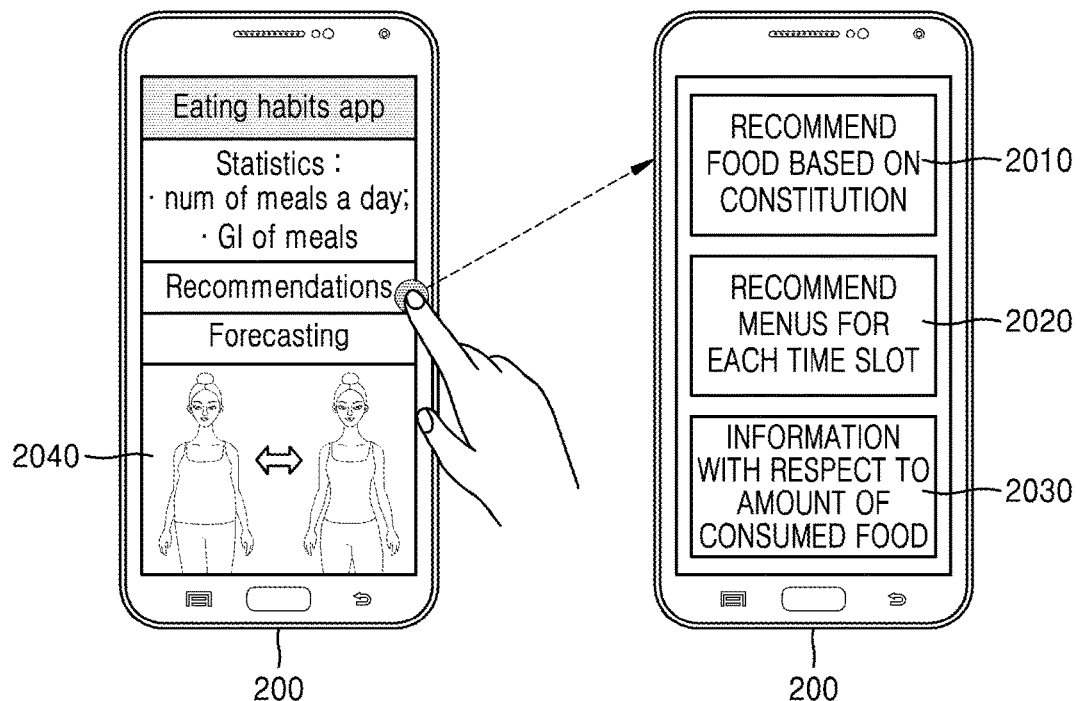
FIG. 20 illustrates a screen, on which information about recommendations for improving eating habits is provided to a user, according to an embodiment.

FIG. 20 illustrates a screen, on which information about recommendations for improving eating habits is provided to a user, according to an embodiment.

Referring to FIG. 20, the external apparatus 200 connected to the wearable apparatus 100 may provide user-personalized eating habits improvement information. For example, the external apparatus 200 may determine information regarding eating habits improvements required by the user, by using information about the number of meals, a GI, eating intervals, eating times, and a blood sugar curve, with respect to the user.

For example, when the number of meals consumed by the user exceeds a standard number of meals, the external apparatus 200 may warn against a level of risk with respect to the number of meals consumed by the user and may provide information for reducing the number of meals.

Also, when a GI of food consumed per meal of the user is greater than a standard GI, the external apparatus 200 may provide information with respect to the GI of the food.

Meanwhile, the external apparatus 200 may generate eating habits information of the user by correcting the GI by analyzing metabolic characteristics information of the user, and based on the generated eating habits information, may recommend (2010) food based on an individual constitution of the user.

Also, when eating habits deviating from a GI within a predetermined regular range are detected, or in the case of a user having a habit of eating at a late time, the external apparatus 200 may recommend (2020) menus for each time slot.

Also, the external apparatus 200 may provide information 2030 with respect to the amount of consumed food (for example, health state information according to the amount of food consumed) to a user, for whom the amount of consumed food is measured to be excessive or insufficient.

The eating habits improvement information provided by the external apparatus 200 may vary based on a health state and the eating habits information of a user. That is, the external apparatus 200 may provide the user-personalized eating habits improvement information. Meanwhile, the external apparatus 200 may provide predetermined information as the eating habits improvement information.

Meanwhile, the external apparatus 200 may provide information 2040 of body-shape prediction based on improvement of eating habits. For example, the external apparatus 200 may provide an image of a user whereby the user is changed to appear slim, rather than a current image of the user.

Figure 21:
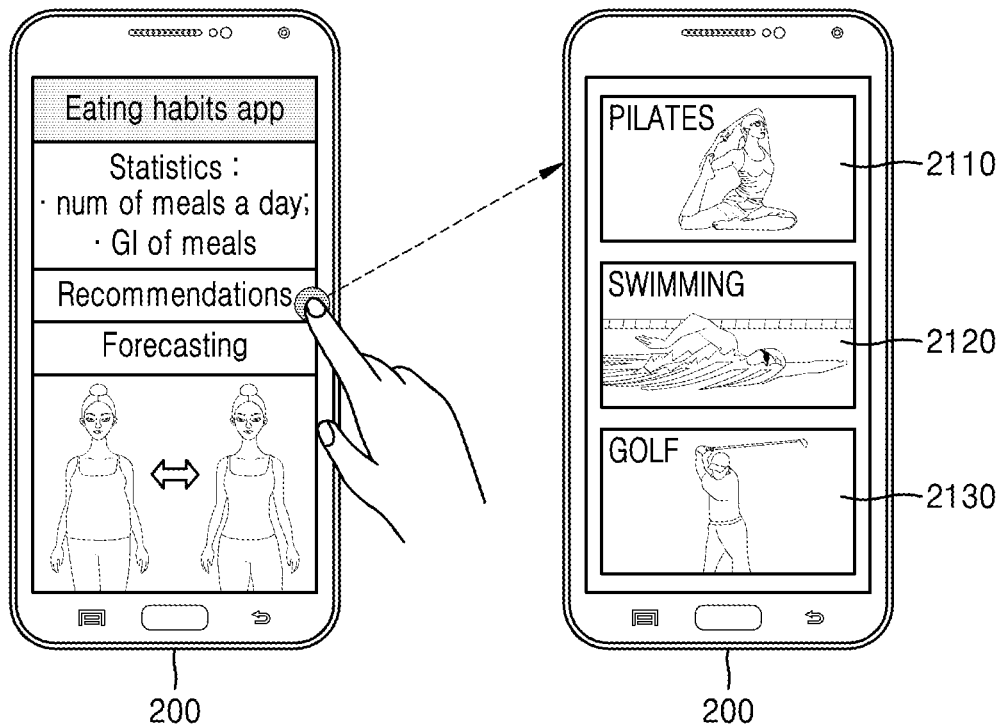
FIG. 21 illustrates a screen, on which information about exercise recommendations is provided to a user, according to an embodiment.

FIG. 21 illustrates a screen, on which information about exercise recommendations is provided to a user, according to an embodiment.

Referring to FIG. 21, the external apparatus 200 connected to the wearable apparatus 100 may recommend an appropriate exercise to a user based on eating habits information of the user. According to an embodiment, the external apparatus 200 may diagnose current eating habits of the user by using at least one of the number of meals consumed by the user over a predetermined time period, eating intervals, eating times, average eating duration time, a blood sugar curve, and a GI corresponding to each meal. The external apparatus 200 may recommend at least one exercise to the user based on the current eating habits. For example, the external apparatus 200 may provide pilates 2110, swimming 2120, or golf 2130 to the user as an exercise recommendation, based on the eating habits information of the user.

The information about exercise recommendations provided by the external apparatus 200 may vary based on a state of the user. Also, the information about exercise recommendations provided by the external apparatus 200 may be received from the wearable apparatus 100.

According to an embodiment, the external apparatus 200 may determine exercise recommendations by taking into account a user preference directly input by the user, a user identification, the age of the user, a physical ability of the user, a season, a place, a time, etc. However, the present disclosure is not limited thereto.

Figure 22:
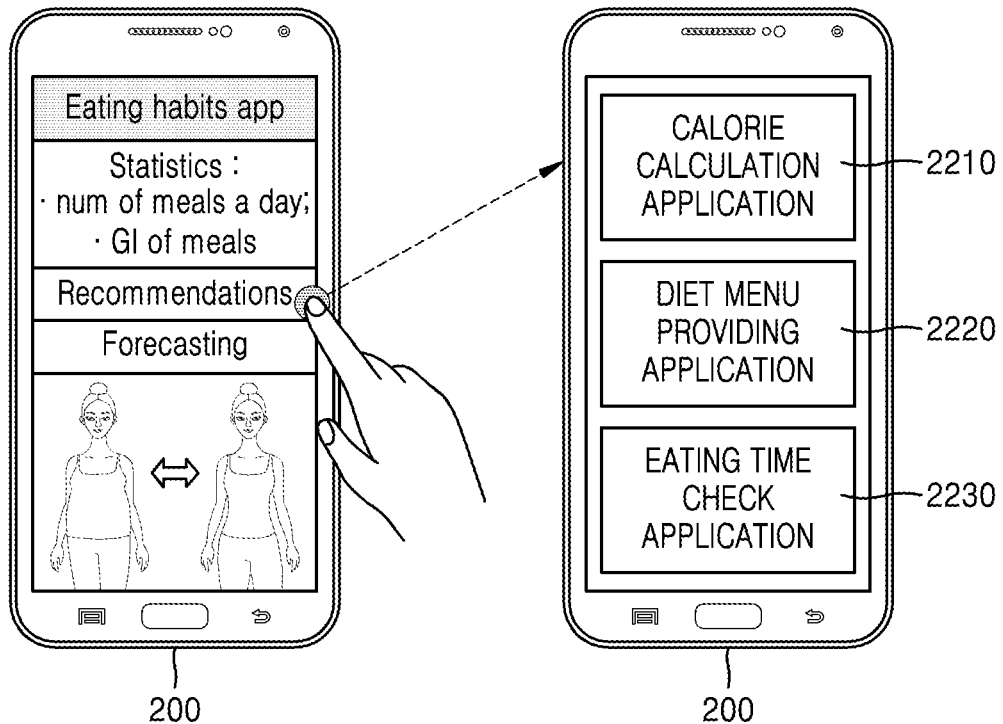
FIG. 22 illustrates a screen, on which an application about eating habits improvement is recommended to a user, according to an embodiment.

FIG. 22 illustrates a screen, on which an application for eating habits improvement is recommended to a user, according to an embodiment.

Referring to FIG. 22, the external apparatus 200 connected to the wearable apparatus 100 may provide an application for recommendations based on eating habits information of the user. The application for recommendations may include, but is not limited to, at least one of a weight management application, a calorie calculation application 2210, a diet application (for example, a diet menu providing application 2220), an exercise management application, and a disease management application.

For example, when a GI corresponding to a meal, in the eating habits information of the user, is determined to be higher than a standard GI, the external apparatus 200 may recommend to the user an application for providing a GI of each of particular types of food.

Alternatively, when a relatively high blood sugar level of the user is sensed against an average eating duration time, the external apparatus 200 may determine that the user eats food hurriedly. The external apparatus 200 may recommend to the user an application 2230 for checking eating times.

Also, according to an embodiment, the external apparatus 200 may recommend an application to the user by taking into account at least one of a user preference directly input by the user, personal identification information of the user, the age of the user, an interest of the user, a search history of the user, other eating habits information of the user, a season, a place, an eating time, and a gradient of a blood sugar curve. However, the present disclosure is not limited thereto.

In FIGS. 20 through 22, the cases in which the external apparatus 200 provides the information about recommendations to the user are described as an example. However, the present disclosure is not limited thereto. The wearable apparatus 100 may directly provide the information about recommendations (for example, information about recommendations for improving eating habits, information about exercise recommendations, or information about application recommendations).

Figure 23:
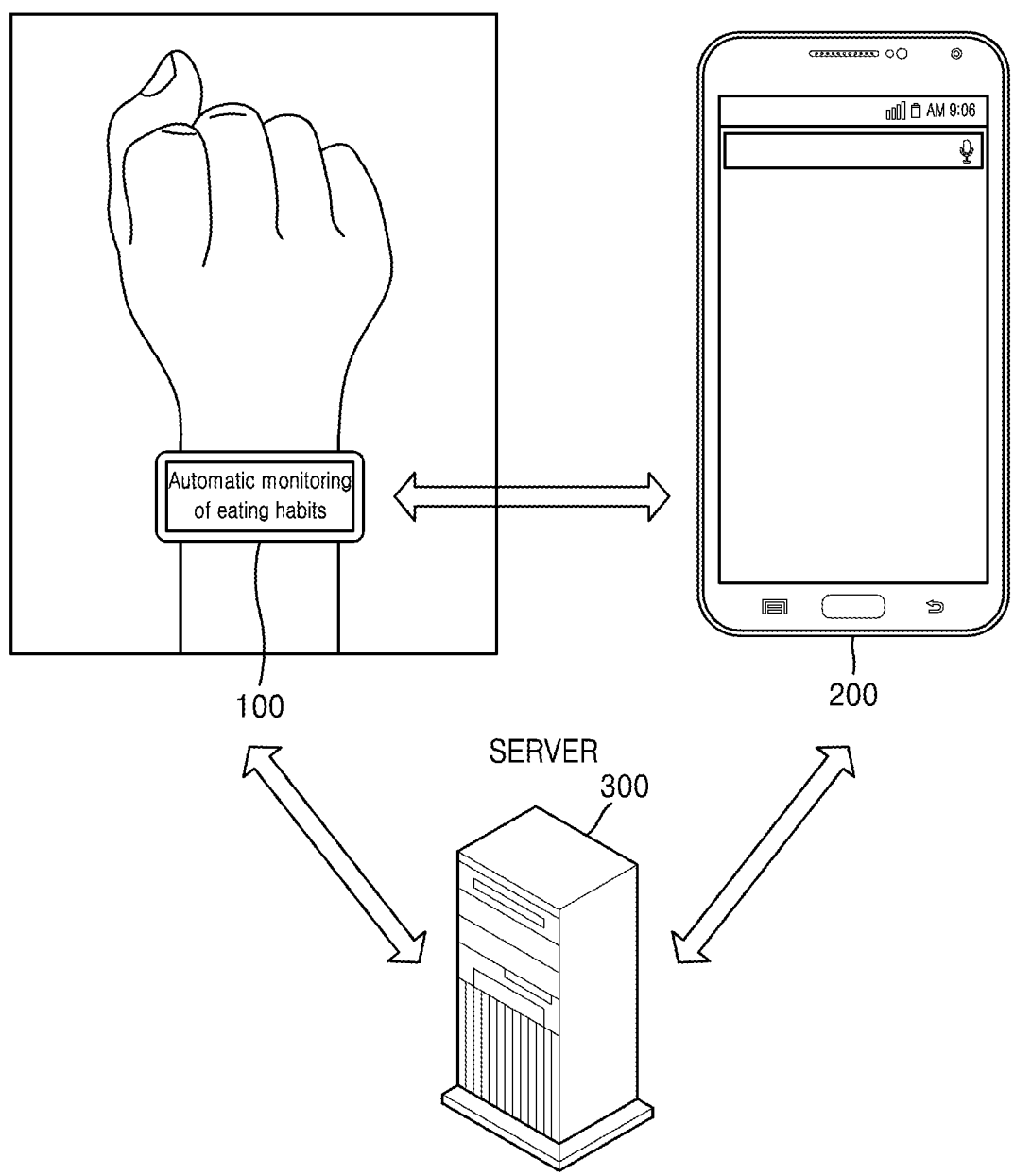
FIG. 23 is a view for describing a system in which a wearable apparatus, an external apparatus, and a server are connected to provide eating habits information, according to an embodiment.

FIG. 23 is a view for describing a system in which the wearable apparatus 100, the external apparatus 200, and the server 300 are connected to provide eating habits information, according to an embodiment.

According to an embodiment, the wearable apparatus 100 may communicate with the external apparatus 200 and the server 300. For example, the wearable apparatus 100 may generate the eating habits information of a user and transmit the eating habits information of the user to the external apparatus 200 and the server 300.

According to another embodiment, the wearable apparatus 100 may measure an impedance signal of the user and transmit the impedance signal to the external apparatus 200 and/or the server 300. The external apparatus 200 and/or the server 300 may generate the eating habits information of the user based on the impedance signal of the user. Here, the external apparatus 200 and/or the server 300 may transmit the eating habits information of the user to the wearable apparatus 100 again. Also, the external apparatus 200 and the server 300 may exchange information with each other.

According to an embodiment, the server 300 and/or the external apparatus 200 may transmit, to the wearable apparatus 100, standard numerical values based on which the eating habits information may be generated. Also, the server 300 and/or the external apparatus 200 may receive and store the eating habits information of the user generated by the wearable apparatus 100.

According to an embodiment, the server 300 and/or the external apparatus 200 may provide eating habits information of another user to the wearable apparatus 100. For example, the server 300 may transmit eating habits information of a child to a terminal or a wearable apparatus of a parent. Also, when the eating habits information of the child corresponds to a predetermined level of risk of eating habits, the server 300 may transmit an alarm message to the wearable apparatus or the terminal of the parent.

According to an embodiment, the wearable apparatus 100 and the external apparatus 200 may directly communicate and exchange data with each other. Also, the wearable apparatus 100 and the external apparatus 200 may exchange data via the server 300.

Figure 24:
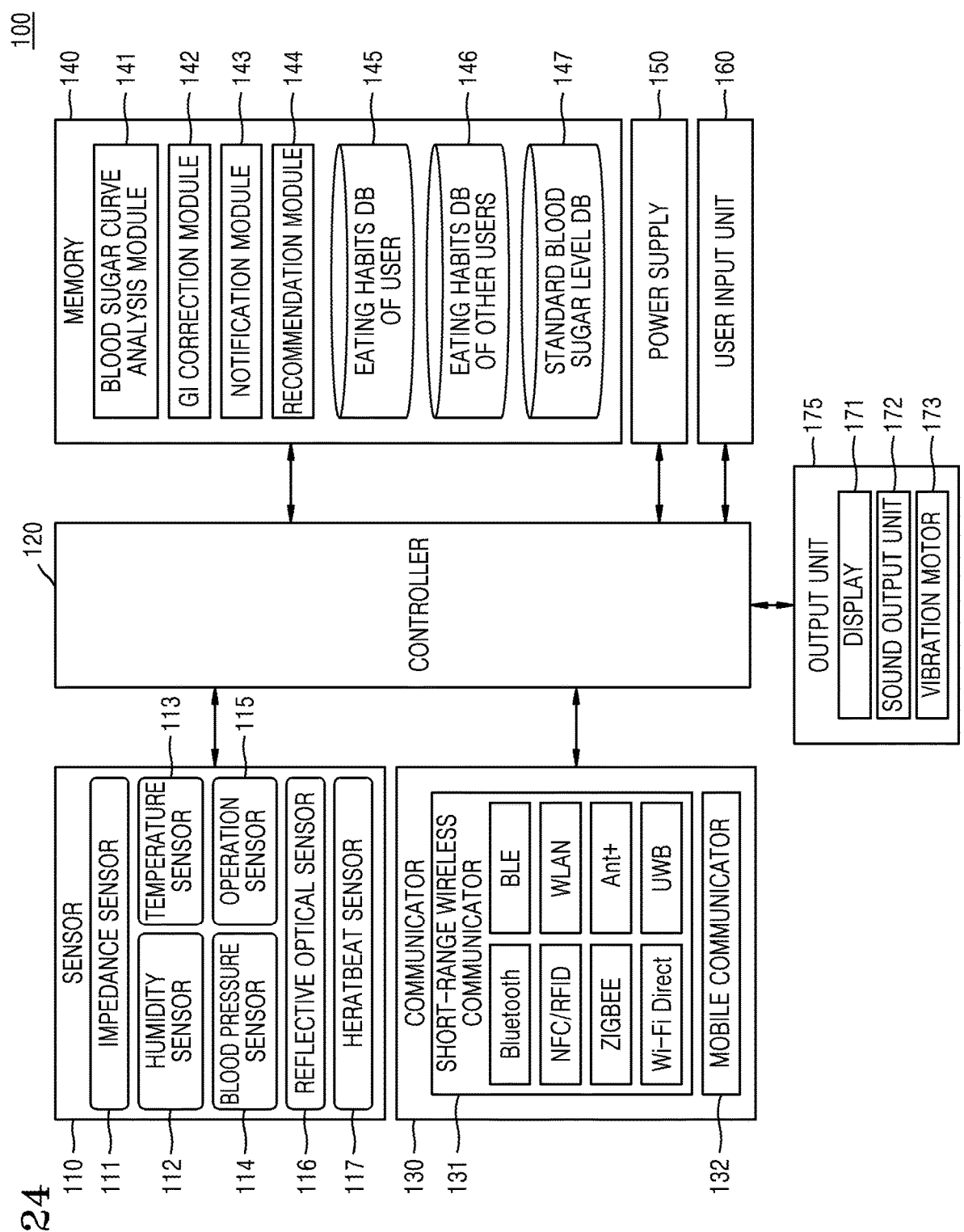
FIG. 24 is a block diagram of detailed components of a wearable apparatus, based on functions, according to an embodiment.

FIG. 24 is a block diagram of detailed components of the wearable apparatus 100, based on functions, according to an embodiment.

As illustrated in FIG. 24, the wearable apparatus 100 according to an embodiment may include a sensor 110, the controller 120, a communicator 130, a memory 140, a power supply 150, a user input unit 160, and an output unit 175. However, not all illustrated components are essential components. The wearable apparatus 100 may be implemented by including more or less components than illustrated.

Hereinafter, the components will be described sequentially.

The sensor 110 may sense a state of the wearable apparatus 100 or a state around the wearable apparatus 100 and may transmit sensed information to the controller 120.

The sensor 110 may include the impedance sensor 111, a humidity sensor 112, a temperature sensor 113, a blood pressure sensor 114, an operation sensor 115, a reflective optical sensor 116, and a heartbeat sensor 117. Also, although not illustrated, the sensor 110 may include, but is not limited to, at least one of a magnetic sensor, an acceleration sensor, an infrared sensor, a gyroscope sensor, a position sensor (for example, a global positioning system (GPS)), an atmospheric sensor, a proximity sensor, and an RGB sensor (an illuminance sensor). A function of each sensor may be intuitively inferred by one of ordinary skill in the art from its name, and thus, its detailed description will be omitted.

The controller 120 may determine the number of meals consumed over a predetermined time period and a GI corresponding to each meal by using a measured impedance signal, and may provide eating habits information of a user based on the number of meals and the GI.

Also, the controller 120 may generate a blood sugar curve by using the measured impedance signal and analyze the blood sugar curve to determine the number of meals consumed over a predetermined time period and the GI corresponding to each meal.

The controller 120 may obtain metabolic characteristics information of the user and may correct the GI by using the metabolic characteristics information. Also, the controller 120 may measure an impedance signal in a body of the user to determine a blood sugar level after consumption of a selected food, and may obtain the metabolic characteristics information of the user based on a result of comparing the determined blood sugar level with a standard blood sugar level of the selected food.

Also, the controller 120 may determine a level of risk of eating habits of the user based on the eating habits information of the user, and when the level of risk of the eating habits of the user is higher than a critical value, the controller 120 may control the output unit 175 to output a warning notification.

Also, the controller 120 may control the user input unit 160 to output at least one of information about recommendations for improving eating habits, information about exercise recommendations, and information about prediction of a body-shape change based on eating habits improvement, based on the eating habits information of the user.

Also, the controller 120 may recommend at least one of a weight management application, a diet application, an exercise management application, and a disease management application, based on the eating habits information of the user.

The communicator 130 may include one or more components configured to enable communication between the wearable apparatus 100 and the external apparatus 200 or between the wearable apparatus 100 and the server 300. For example, the communicator 130 may include a short-range wireless communicator 131 and a mobile communicator 132.

The short-range wireless communicator 131 may include, but is not limited to, Bluetooth, BLE, NFC, WLAN (Wifi), Zigbee, infrared data association (IrDA), Wi-fi direct (WFD), UWB, Ant+, etc.

The mobile communicator 132 may transmit and receive a wireless signal to and from at least one of a base station, an external terminal, and a server, in a mobile communication network. Here, the wireless signal may include a sound call signal, a videotelephony call signal, or data of various formats based on text/multimedia message transmission and reception.

The memory 140 may store programs for processing and controlling of the controller 120, and may store input/output data (for example, an application, sound data, impedance data, video data, information about applications, information about a level of risk of eating habits, etc.).

The memory 140 may include at least one type of storage medium from among a flash memory type, a hard disk type, a multimedia card micro type, a card type (for example, SD or XD memory), random-access memory (RAM), static RAM (SRAM), read-only memory (ROM), electrically erasable programmable ROM (EEPROM), programmable ROM (PROM), a magnetic memory, a magnetic disk, and an optical disk. Also, the wearable apparatus 100 may operate a web storage or a cloud server configured to perform a storage function of the memory 140 on the Internet.

The programs stored in the memory 140 may be divided into a plurality of modules based on their functions. For example, the programs may include a blood sugar curve analysis module 141, a GI correction module 142, a notification module 143, a recommendation module 144, an eating habits database (DB) of a user 145, an eating habits DB of other users 146, and a standard blood sugar level DB 147.

The blood sugar curve analysis module 141 may generate a blood sugar curve via an impedance signal of the user collected by the impedance sensor 111 and may analyze the blood sugar curve.

The GI correction module 142 may correct the GI based on information of the user, for example, at least one of body temperature information, sweating amount information, skin characteristics information, heartbeat information, blood pressure information, activity information, individual metabolic characteristics information, and metabolism coefficient information of the user.

The notification module 143 may control the output unit 175 to output a warning notification when the level of risk of eating habits of the user is higher than a predetermined critical value.

The recommendation module 144 may control the output unit 170 to recommend to the user necessary information, necessary applications, or exercises, based on the eating habits information of the user.

The eating habits DB of the user 145 may store eating habits data of a user determined as a main user of the wearable apparatus 100. The eating habits DB of the user 145 may back-up or format the eating habits data of the user, based on a cycle determined in the wearable apparatus 100.

The eating habits DB of other users 146 may store eating habits data of other users, received from the external apparatus 200 and the server 300. For example, the eating habits DB of other users 146 may store eating habits data of families of the main user.

The standard blood sugar level DB 147 may include information about the standard GIs, based on which the eating habits information of the user and the level of risk of the eating habits of the user may be determined. The information about the standard GIs may be received from the external apparatus 200 and the server 300. However, the present disclosure is not limited thereto.

The user input unit 160 may denote a device via which a user inputs data to control the wearable apparatus 100. For example, the user input unit 160 may include, but is not limited to, a key pad, a dome switch, a touch pad (a touch capacitance method, a pressure resistive method, an infrared sensing method, a surface ultrasonic conductive method, an integral tension measuring method, a piezo effect method, etc.), a jog wheel, a jog switch, etc.

The output unit 175 may be configured to output an audio signal, a video signal, or a vibration signal, and may include a display 171, a sound output unit 172, a vibration motor 173, etc.

The display 171 may visually output the eating habits information of the user, and a blood sugar curve of the user, an alarm message, etc.

When a layered structure including the display unit 171 and a touch pad forms a touch screen, the display unit 171 may be used as an input device, in addition to an output device. The display unit 171 may include at least one of a liquid crystal display (LCD), a thin film transistor LCD, an organic light-emitting diode (OLED) display, a flexible display, a three-dimensional (3D) display, and an electrophoretic display. The wearable apparatus 100 may include two or more display units 171, according to an embodiment.

The sound output unit 172 may output audio data received from the communicator 130 or stored in the memory 140. Also, the sound output unit 172 may output sound signals associated with functions (for example, a call signal reception sound, a message reception sound, a notification sound, etc.) performed by the wearable apparatus 100. The sound output unit 172 may include a speaker, a buzzer, etc.

The vibration motor 173 may output a vibration signal. For example, the vibration motor 173 may output a vibration signal corresponding to an output of audio data or video data (for example, a call signal reception sound, a message reception sound, or the like). Also, the vibration motor 173 may output a vibration signal when a touch is input on a touch screen.

Figure 25:
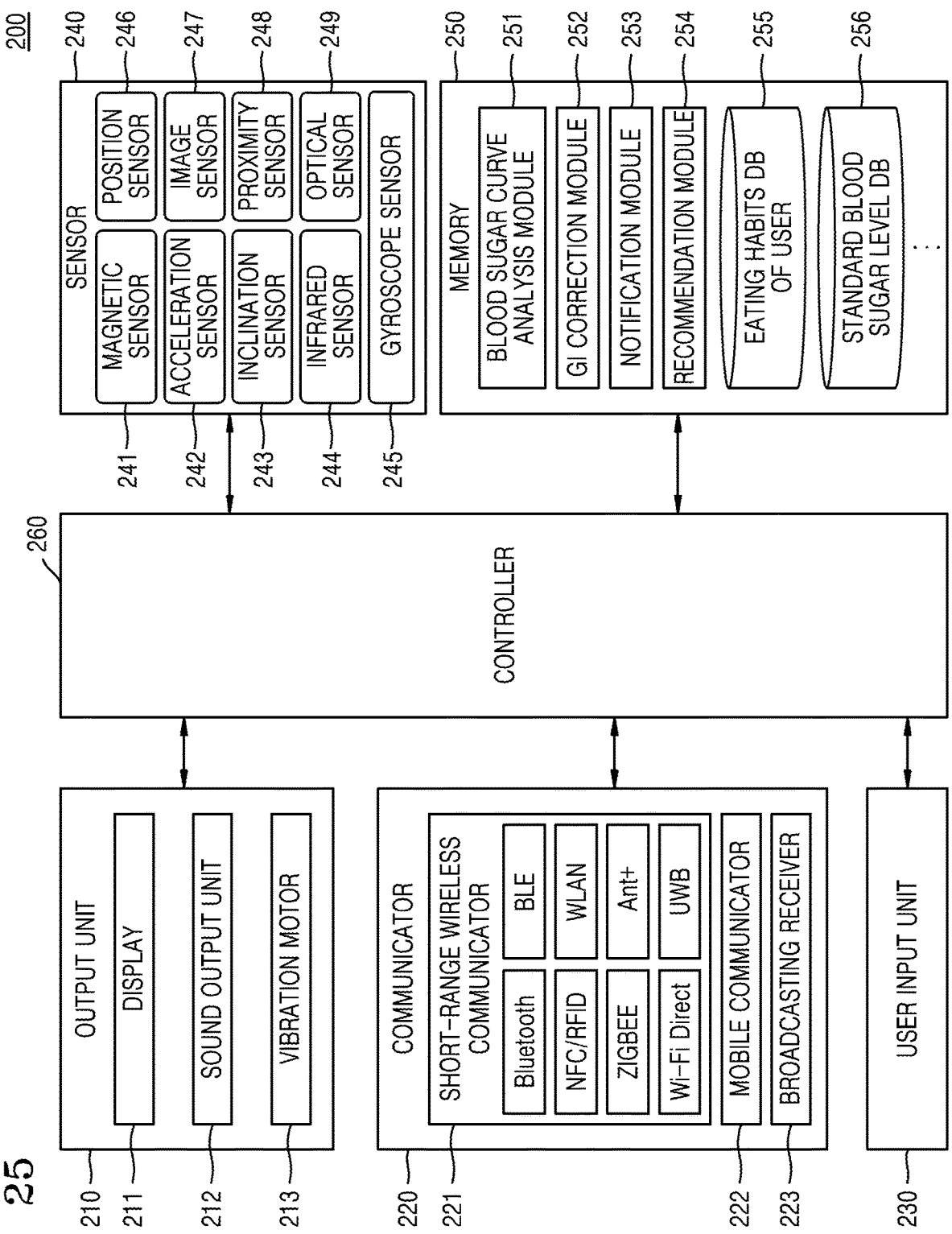
FIG. 25 is a block diagram of components of an external apparatus, based on functions, according to an embodiment.

FIG. 25 is a block diagram of components of the external apparatus 200, based on functions, according to an embodiment.

As illustrated in FIG. 25, the external apparatus 200 according to an embodiment may include an output unit 210, a communicator 220, a user input unit 230, a controller 260, a sensor 240, and a memory 250. However, not all illustrated components are essential components. The external apparatus 200 may be implemented by including more or less components than illustrated.

The output unit 210 may be configured to output an audio signal, a video signal, or a vibration signal, and may include a display 211, a sound output unit 212, a vibration motor 213, etc.

The display 211 may visually output the eating habits information of the user, and a blood sugar curve of the user, an alarm message, etc.

The sound output unit 212 may output audio data received from the communicator 220 or stored in the memory 250. Also, the sound output unit 212 may output sound signals associated with functions (for example, a call signal reception sound, a message reception sound, a notification sound, etc.) performed by the external apparatus 200. The sound output unit 212 may include a speaker, a buzzer, etc.

The vibration motor 213 may output a vibration signal. For example, the vibration motor 213 may output a vibration signal corresponding to an output of audio data or video data (for example, a call signal reception sound, a message reception sound, or the like). Also, the vibration motor 213 may output a vibration signal when a touch is input on the touch screen.

The communicator 220 may include one or more components configured to enable communication between the external apparatus 200 and the wearable apparatus 100 or between the external apparatus 200 and the server 300. For example, the communicator 220 may include a short-range wireless communicator 221, a mobile communicator 222, and a broadcasting receiver 223.

The short-range wireless communicator 221 may include, but is not limited to, Bluetooth, BLE, NFC, WLAN (Wifi), Zigbee, IrDA, WFD, UWB, Ant+, etc.

The mobile communicator 222 may transmit and receive a wireless signal to and from at least one of a base station, an external terminal, and a server, in a mobile communication network. Here, the wireless signal may include a sound call signal, a videotelephony call signal, or data of various formats based on text/multimedia message transmission and reception.

The broadcasting receiver 223 may receive a broadcasting signal and/or information related to broadcasting from the outside via broadcasting channels. The broadcasting channels may include a satellite channel, a ground-wave channel, etc. According to an embodiment, the external apparatus 200 may not include the broadcasting receiver 223.

The user input unit 230 may denote a device via which a user inputs data to control the external apparatus 200. For example, the user input unit 230 may include, but is not limited to, a key pad, a dome switch, a touch pad (a touch capacitance method, a pressure resistive method, an infrared sensing method, a surface ultrasonic conductive method, an integral tension measuring method, a piezo effect method, etc.), a jog wheel, a jog switch, etc.

According to an embodiment, the user input unit 230 may receive an input of selecting a playback function button or an edit function button, via a virtual control panel.

The playback function button may include at least one of a playback button, a pause button, a fast-forward button, a rewind button, and a playback speed control button. The edit function button may include at least one of an execution undo button, a redo button, a text recognition button, an addition button, and an exchange button. The control panel may include a search bar for searching for a section of note content.

The controller 260 may generally control general operations of the external apparatus 200. For example, the controller 260 may generally control the output unit 210, the communicator 220, the user input unit 230, the sensor 240, the memory 250, etc. by executing programs stored in the memory 250.

The sensor 240 may include, but is not limited to, at least one of a magnetic sensor 241, an acceleration sensor 242, an inclination sensor 243, an infrared sensor 244, a gyroscope sensor 245, a position sensor (for example, a GPS) 246, an image sensor 247, a proximity sensor 248, and an optical sensor 249. A function of each of the sensors may be intuitively inferred by one of ordinary skill in the art from its name, and thus, its detailed description will be omitted.

The memory 250 may store the programs for processing and controlling of the controller 260, and may store input/output data (for example, an application, a user impedance signal, a blood sugar level of a user, a standard blood sugar level, a level of risk of eating habits, information about other users, user identification information, image information, sound information, note content, multimedia content, transcripts, etc.).

The memory 250 may include at least one type of storage medium from among a flash memory type, a hard disk type, a multimedia card micro type, a card type (for example, SD or XD memory), RAM, SRAM, ROM, EEPROM, PROM, a magnetic memory, a magnetic disk, and an optical disk.

The programs stored in the memory 250 may be divided into a plurality of modules based on their functions. For example, the programs may include a blood sugar curve analysis module 251, a GI correction module 252, a notification module 253, a recommendation module 254, an eating habits DB of a user 255, and a standard blood sugar level DB 256. Descriptions of the programs stored in the memory 250 are the same as those of the programs stored in the memory 140 of the wearable apparatus 100, and thus, they will be omitted.

Figure 26:
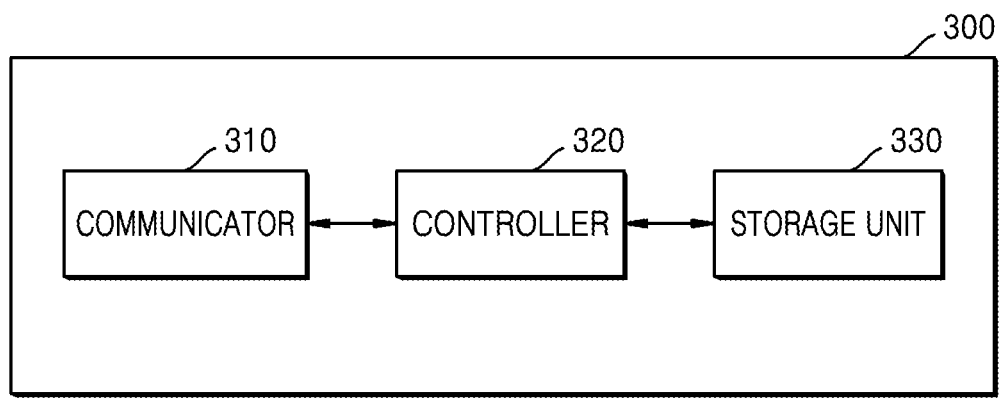
FIG. 26 is a block diagram of components of a server, based on functions, according to an embodiment.

FIG. 26 is a block diagram of components of the server 300, based on functions, according to an embodiment.

As illustrated in FIG. 26, the server 300 according to an embodiment may include a communicator 310, a controller 320, and a storage unit 330. However, not all illustrated components are essential components. The server 300 may be implemented by including more or less components than illustrated.

The communicator 310 may include one or more components configured to enable communication between the server 300 and the wearable apparatus 100 or between the server 300 and the external apparatus 200. For example, the server 300 may receive eating habits information of a user or data based on an impedance signal of the user, from the wearable apparatus 100, via the communicator 310. According to an embodiment, the server 300 may transmit, to the external apparatus 200, the eating habits information of the user received from the wearable apparatus 100 via the communicator 310, or may store the eating habits information of the user in the storage unit 330.

The controller 320 may generally control general operations of the server 300. For example, the controller 320 may generally control the communicator 310 by executing programs stored in the storage unit 330.

The storage unit 330 may store the programs for processing and controlling of the controller 320, and may store information with respect to data and signals input/output via the communicator 310.

The method according to an embodiment may be implemented as computer commands which may be executed by various computer means, and recorded on a non-transitory computer-readable recording medium. The non-transitory computer-readable recording medium may include program commands, data files, data structures, or a combination thereof. The program commands recorded on the non-transitory computer-readable recording medium may be specially designed and constructed for the present disclosure or may be known to and usable by one of ordinary skill in a field of computer software. Examples of the non-transitory computer-readable medium include storage media such as magnetic media (e.g., hard discs, floppy discs, or magnetic tapes), optical media (e.g., compact disc read-only memories (CD-ROMs), or digital versatile discs (DVDs)), magneto-optical media (e.g., floptical discs), and hardware devices that are specially configured to store and carry out program commands (e.g., ROMs, RAMs, or flash memories). Examples of the program commands include a high-level programming language code that may be executed by a computer using an interpreter as well as a machine language code made by a complier.

The scope of the present disclosure is indicated by the claims rather than by the detailed description of the disclosure, and it should be understood that the claims and all modifications or modified forms drawn from the concept of the claims are included in the scope of the present disclosure.

The invention claimed is:

1. A wearable apparatus comprising:
    an impedance sensor configured to measure an impedance signal in a body of a user; and
    a controller configured to:
        monitor changes in the impedance signal,
        determine, by using the measured impedance signal, a number of meals consumed during a certain time period and a glycemic index (GI) corresponding to each meal,
        provide eating habits information of the user based on the determined number of meals and the determined GI for each meal,
        determine a level of risk of eating habits of the user based on the eating habits information of the user, and
        control an output unit to output a warning notification when the level of risk of the eating habits of the user is greater than a critical value,
    wherein the impedance sensor comprises:
        a signal source configured to generate an alternating current (AC) power supply having at least two frequency ranges;
        a probe configured to receive the AC power supply and to transmit an AC signal to the body of the user in at least two directions using at least two tetrapolar circuits included in the probe, including a first direction based on muscle fibers and a second direction traversing the muscle fibers; and
        a signal sensor configured to receive the AC signal transmitted by the probe through the body of the user, and to convert the received AC signal into the impedance signal.

2. The wearable apparatus of claim 1, wherein the controller is further configured to generate a blood sugar curve by using the measured impedance signal and analyze the generated blood sugar curve to determine the number of meals for the certain time period and the GI corresponding to each meal.

3. The wearable apparatus of claim 1, further comprising:
    at least one of a temperature sensor configured to measure a body temperature of the user, a humidity sensor configured to measure an amount of sweating of the user, a reflective optical sensor configured to measure a skin characteristic of the user, a heartbeat sensor configured to measure a heartbeat of the user, a blood pressure sensor configured to measure a blood pressure of the user, and an operation sensor configured to measure an activity of the user,
    wherein the controller is further configured to correct the determined GI by taking into account at least one of body temperature information, sweating amount information, skin characteristics information, heartbeat information, blood pressure information, and activity information of the user.

4. The wearable apparatus of claim 1, wherein the controller is further configured to obtain metabolic characteristics information of the user and to correct the determined GI by using the metabolic characteristics information.

5. The wearable apparatus of claim 4, further comprising:
    a user input unit configured to receive, from the user, an input of selecting food to be consumed,
    wherein the controller is further configured to determine a blood sugar level corresponding to the selected food by measuring the impedance signal in the body of the user, and to obtain the metabolic characteristics information of the user based on a result of comparing the determined blood sugar level with a standard blood sugar level of the selected food.

6. The wearable apparatus of claim 1, wherein the controller is further configured to control an output unit to output at least one of information about recommendations for improving eating habits, information about exercise recommendations, and information about prediction of a body-shape change based on eating habits improvement, based on the eating habits information of the user.

7. The wearable apparatus of claim 1, wherein the controller is further configured to recommend at least one of a weight management application, a diet application, an exercise management application, and a disease management application, based on the eating habits information of the user.

8. The wearable apparatus of claim 1, further comprising:
    a communicator configured to transmit the eating habits information of the user to an external apparatus.

9. A method of providing eating habits information, the method comprising:
    measuring an impedance signal in a body of a user by using an impedance sensor comprising a signal source configured to generate an alternating current (AC) power supply having at least two frequency ranges, a probe configured to receive the AC power supply and to transmit an AC signal to the body of the user in at least two directions using at least two tetrapolar circuits included in the probe, including a first direction based on muscle fibers and a second direction traversing the muscle fibers; and a signal sensor configured to receive the AC signal transmitted by the probe through the body of the user, and to convert the received AC signal into the impedance signal;
    monitoring changes in the impedance signal by using a controller;
    determining, by using the controller, a number of meals for a certain time period and a glycemic index (GI) corresponding to each meal, by using the measured impedance signal; and
    providing the eating habits information of the user based on the determined number of meals and the GI;
    determining a level of risk of eating habits of the user based on the eating habits information of the user by using the controller, and
    controlling an output unit to output a warning notification when the level of risk of the eating habits of the user is greater than a critical value.

10. The method of claim 9, wherein the eating habits information of the user comprises at least one of information about the number of meals for the certain time period, information about eating intervals, information about eating times, information about an average eating duration time, information about a blood sugar curve, and information about a GI corresponding to each meal.

11. The method of claim 9, wherein the determining of the number of meals and the GI comprises:
generating a blood sugar curve by using the measured impedance signal; and
determining the number of meals for the certain time period and the GI corresponding to each meal, by analyzing the blood sugar curve.

12. The method of claim 9, further comprising:
correcting the determined GI by taking into account at least one of body temperature information, sweating amount information, skin characteristics information, heartbeat information, blood pressure information, and activity information of the user.

13. The method of claim 9, further comprising:
obtaining metabolic characteristics information of the user; and
correcting the GI by using the metabolic characteristics information.

14. The method of claim 13, wherein the obtaining of the metabolic characteristics information of the user comprises:
receiving, from the user, an input of selecting food to be consumed;
determining a blood sugar level corresponding to the selected food by measuring the impedance signal in the body of the user; and
obtaining the metabolic characteristics information of the user based on a result of comparing the determined blood sugar level with a standard blood sugar level of the selected food.

15. The method of claim 9, further comprising:
based on the eating habits information of the user, outputting at least one of information about recommendations for improving eating habits, information about exercise recommendations, information about prediction of a body-shape change based on eating habits improvement, and information about application recommendations.

16. The method of claim 9, further comprising:
transmitting the eating habits information of the user to an external apparatus.

17. A computer program product including a non-transitory computer-readable recording medium storing a plurality of instructions for executing a method of claim 9, and that, when read and executed by a processor.

* * * * *